(12) United States Patent
Tegg et al.

(10) Patent No.: US 9,023,033 B2
(45) Date of Patent: May 5, 2015

(54) MAGNETICALLY GUIDED CATHETERS

(75) Inventors: Troy T. Tegg, Elk River, MN (US); James V. Kauphusman, Champlin, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1242 days.

(21) Appl. No.: 12/850,485

(22) Filed: Aug. 4, 2010

(65) Prior Publication Data

US 2012/0035605 A1 Feb. 9, 2012

(51) Int. Cl.
*A61B 18/12* (2006.01)
*A61M 25/01* (2006.01)
*A61B 5/042* (2006.01)
*A61B 5/06* (2006.01)
*A61B 5/00* (2006.01)
*A61B 18/14* (2006.01)
*A61B 18/00* (2006.01)
*A61B 19/00* (2006.01)

(52) U.S. Cl.
CPC .......... *A61M 25/0127* (2013.01); *A61B 5/0422* (2013.01); *A61B 5/062* (2013.01); *A61B 5/6852* (2013.01); *A61B 18/1492* (2013.01); *A61B 2018/00011* (2013.01); *A61B 2018/00029* (2013.01); *A61B 2018/00577* (2013.01); *A61B 2019/2253* (2013.01); *A61B 2019/5251* (2013.01); *A61B 2218/002* (2013.01); *A61M 25/0158* (2013.01); *A61M 2025/0166* (2013.01)

(58) Field of Classification Search
USPC ......................................................... 606/41
See application file for complete search history.

(56) References Cited

U.S. PATENT DOCUMENTS

| | | | |
|---|---|---|---|
| 3,674,014 | A | 7/1972 | Tillander |
| 3,935,766 | A | 2/1976 | Masters |
| 4,809,713 | A | 3/1989 | Grayzel |
| 4,945,912 | A | 8/1990 | Langberg |
| 5,056,517 | A | 10/1991 | Fenici |
| 5,279,299 | A | 1/1994 | Imran |
| 5,363,861 | A | 11/1994 | Edwards et al. |
| 5,378,230 | A | 1/1995 | Mahurkar |
| 5,542,938 | A | 8/1996 | Avellanet et al. |
| 5,545,200 | A | 8/1996 | West et al. |
| 5,706,827 | A | 1/1998 | Ehr et al. |
| 5,782,810 | A | 7/1998 | O'Donnell |
| 5,788,713 | A | 8/1998 | Dubach et al. |
| 5,911,720 | A | 6/1999 | Bourne et al. |

(Continued)

FOREIGN PATENT DOCUMENTS

| WO | 96/34652 | 11/1996 |
|---|---|---|
| WO | 2005/094661 | 10/2005 |

OTHER PUBLICATIONS

"International Search Report and Written Opinion", PCT/US2011/040425 Oct. 6, 2011.

*Primary Examiner* — Aaron Roane
(74) *Attorney, Agent, or Firm* — Dykema Gossett PLLC

(57) ABSTRACT

A magnetically-guided catheter includes a tip positioning magnet in the distal electrode assembly configured to interact with externally applied magnetic fields for magnetically-guided movement. A magnetically-guided mapping catheter includes an electrically-conductive capsule in the form of a casing that includes a distal ablation surface and isolates the positioning magnet from bio-fluids to prevent corrosion. An open irrigation ablation catheter includes an isolated manifold that isolates the positioning magnet from contact with irrigation fluid to prevent corrosion.

16 Claims, 20 Drawing Sheets

(56) References Cited

U.S. PATENT DOCUMENTS

| | | | |
|---|---|---|---|
| 5,951,471 A | 9/1999 | de la Rama et al. | |
| 6,001,095 A | 12/1999 | de la Rama et al. | |
| 6,015,414 A | 1/2000 | Werp et al. | |
| 6,126,647 A | 10/2000 | Posey et al. | |
| 6,185,448 B1 | 2/2001 | Borovsky | |
| 6,217,573 B1 | 4/2001 | Webster | |
| 6,233,476 B1 | 5/2001 | Strommer et al. | |
| 6,235,024 B1 | 5/2001 | Tu | |
| 6,251,134 B1 | 6/2001 | Alt | |
| 6,273,876 B1 | 8/2001 | Klima et al. | |
| 6,292,678 B1 | 9/2001 | Hall et al. | |
| 6,356,790 B1 | 3/2002 | Maguire et al. | |
| 6,385,472 B1 | 5/2002 | Hall et al. | |
| 6,464,632 B1 | 10/2002 | Taylor et al. | |
| 6,475,223 B1 | 11/2002 | Werp et al. | |
| 6,493,590 B1 | 12/2002 | Wessman et al. | |
| 6,524,303 B1 | 2/2003 | Garibaldi | |
| 6,544,270 B1 | 4/2003 | Zhang | |
| 6,605,087 B2 | 8/2003 | Swartz et al. | |
| 6,611,699 B2 | 8/2003 | Messing | |
| 6,662,034 B2 | 12/2003 | Segner et al. | |
| 6,669,692 B1 | 12/2003 | Nelson et al. | |
| 6,690,963 B2 | 2/2004 | Ben-Haim et al. | |
| 6,730,082 B2 | 5/2004 | Messing et al. | |
| 6,733,497 B2 | 5/2004 | Messing et al. | |
| 6,740,083 B2 | 5/2004 | Messing et al. | |
| 6,755,816 B2 | 6/2004 | Ritter et al. | |
| 6,780,183 B2 | 8/2004 | Jimenez, Jr. et al. | |
| 6,980,843 B2 | 12/2005 | Eng | |
| 7,137,395 B2 | 11/2006 | Fried et al. | |
| 7,197,354 B2 | 3/2007 | Sobe | |
| 7,211,082 B2 | 5/2007 | Hall et al | |
| 7,263,397 B2 | 8/2007 | Hauck et al. | |
| 7,276,044 B2 | 10/2007 | Ferry et al. | |
| 7,280,863 B2 | 10/2007 | Shachar | |
| 7,341,063 B2 | 3/2008 | Garbibaldi et al. | |
| 7,386,339 B2 | 6/2008 | Strommer et al. | |
| 7,536,218 B2 | 5/2009 | Govari et al. | |
| 2001/0012956 A1 | 8/2001 | Behl et al. | |
| 2001/0047129 A1* | 11/2001 | Hall et al. | 600/374 |
| 2002/0058866 A1 | 5/2002 | Segner et al. | |
| 2002/0072662 A1 | 6/2002 | Hall et al. | |
| 2003/0125752 A1 | 7/2003 | Werp et al. | |
| 2003/0176766 A1 | 9/2003 | Long et al. | |
| 2004/0015215 A1 | 1/2004 | Fredricks et al. | |
| 2004/0019447 A1 | 1/2004 | Shachar | |
| 2004/0158142 A1 | 8/2004 | Hall et al. | |
| 2004/0204671 A1 | 10/2004 | Stubbs et al. | |
| 2004/0231683 A1 | 11/2004 | Eng et al. | |
| 2004/0242995 A1 | 12/2004 | Maschke | |
| 2004/0243143 A1 | 12/2004 | Corcoran et al. | |
| 2004/0267106 A1 | 12/2004 | Segner et al. | |
| 2005/0004563 A1 | 1/2005 | Racz et al. | |
| 2005/0054989 A1 | 3/2005 | McGuckin et al. | |
| 2005/0096589 A1 | 5/2005 | Shachar | |
| 2005/0174004 A1 | 8/2005 | Takehara et al. | |
| 2005/0197633 A1 | 9/2005 | Schwartz et al. | |
| 2005/0245846 A1 | 11/2005 | Casey | |
| 2005/0272975 A1 | 12/2005 | McWeeney et al. | |
| 2006/0064123 A1 | 3/2006 | Bonnette et al. | |
| 2006/0114088 A1 | 6/2006 | Shachar | |
| 2006/0116633 A1 | 6/2006 | Shachar | |
| 2006/0116634 A1 | 6/2006 | Shachar | |
| 2006/0149192 A1 | 7/2006 | Deniega et al. | |
| 2006/0200191 A1 | 9/2006 | Zadno-Azizi | |
| 2006/0287650 A1 | 12/2006 | Cao et al. | |
| 2007/0016006 A1 | 1/2007 | Shachar | |
| 2007/0016131 A1 | 1/2007 | Munger et al. | |
| 2007/0066878 A1 | 3/2007 | Worley et al. | |
| 2007/0073268 A1 | 3/2007 | Goble et al. | |
| 2007/0197891 A1* | 8/2007 | Shachar et al. | 600/374 |
| 2008/0027313 A1 | 1/2008 | Shachar | |
| 2008/0039705 A1 | 2/2008 | Viswanathan | |
| 2008/0091193 A1 | 4/2008 | Kauphusman et al. | |
| 2008/0249395 A1 | 10/2008 | Shachar et al. | |
| 2008/0297287 A1 | 12/2008 | Shachar et al. | |
| 2008/0312530 A1* | 12/2008 | Malackowski et al. | 600/426 |
| 2009/0171272 A1 | 7/2009 | Tegg et al. | |
| 2009/0171348 A1 | 7/2009 | Guo et al. | |
| 2009/0306655 A1 | 12/2009 | Stangenes et al. | |
| 2010/0174177 A1 | 7/2010 | Wu | |

* cited by examiner

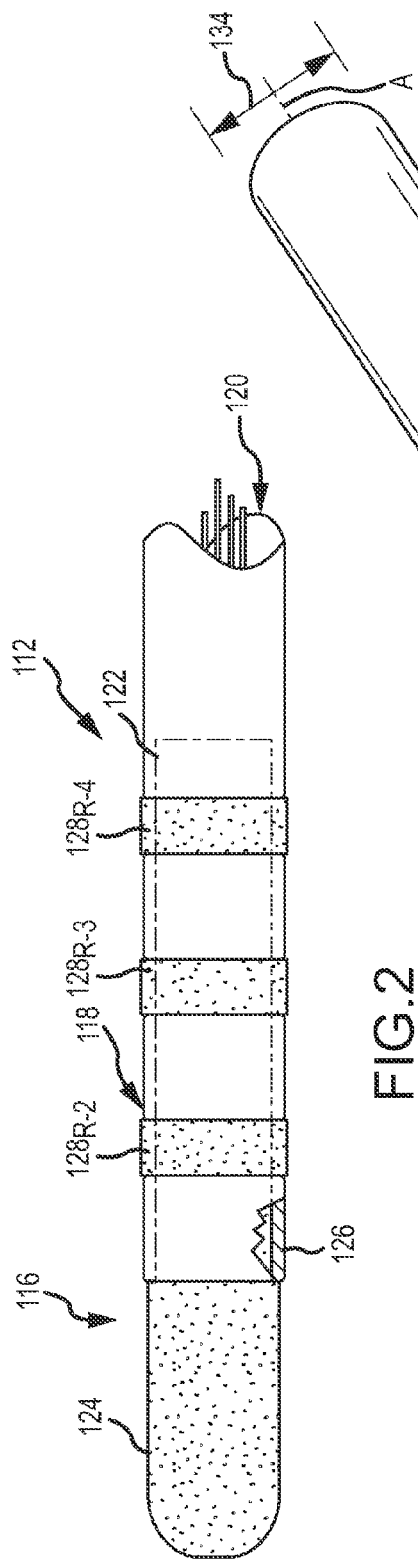
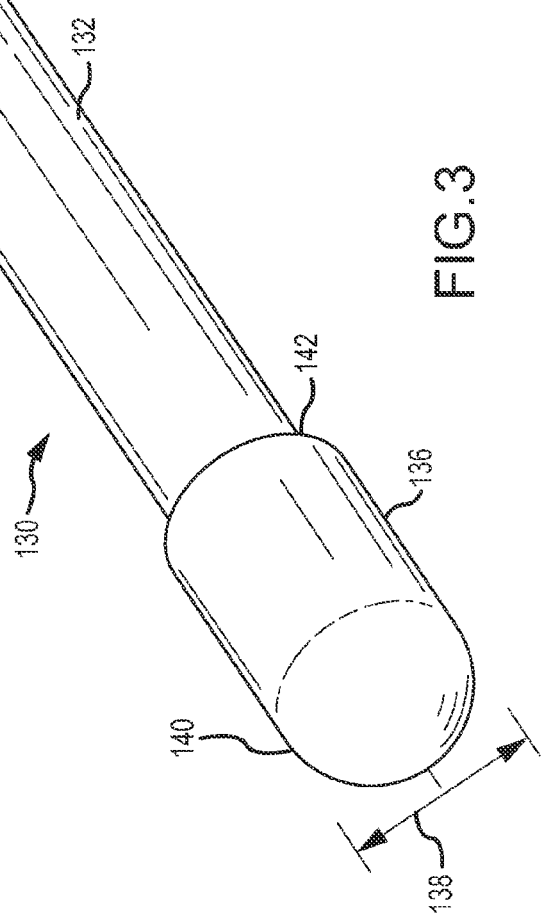

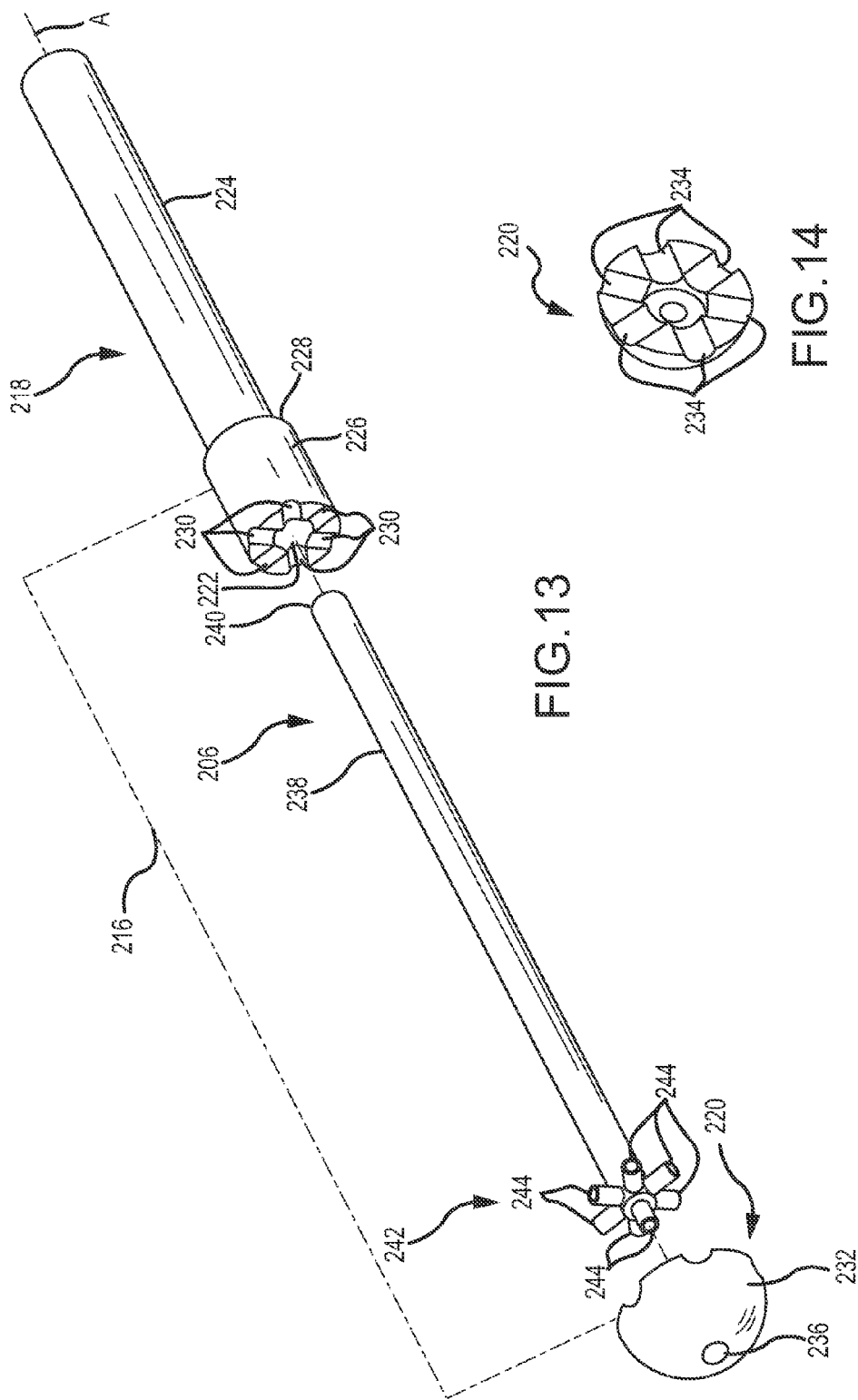

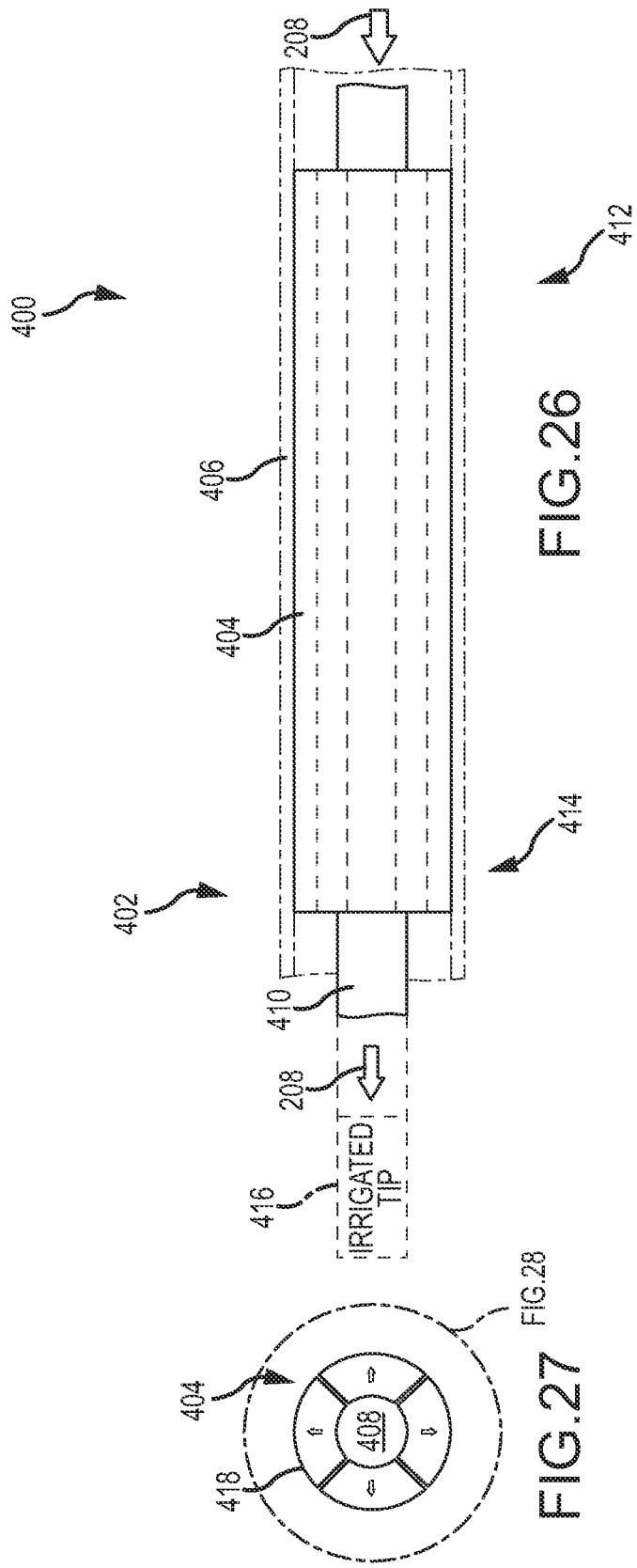

MAGNETICALLY GUIDED CATHETERS

BACKGROUND OF THE INVENTION a. Field of the Invention

The present invention relates generally to medical instruments, and more specifically, to catheters navigable within the body of a patient using externally applied magnetic fields.

b. Background Art

Electrophysiology (EP) catheters have been used for an ever-growing number of procedures. For example, catheters have been used for diagnostic, therapeutic, mapping and ablative procedures, to name just a few examples. Typically, a catheter is manipulated through the patient's vasculature to the intended site, for example, a site within the patient's heart, and carries one or more electrodes, which may be used for mapping, ablation, diagnosis, or other treatments. Precise positioning of the catheters within the body of the patient is desirable for successful completion of the above procedures. In general, such catheters may be complex in their construction and therefore difficult (and expensive) to manufacture.

To position a catheter within the body at a desired site, some type of navigation must be used, such as using mechanical steering features incorporated into the catheter (or an introducer sheath). Another approach has been developed, namely, providing magnetically guided catheter devices that are navigated through the patient's body using externally-generated magnetic fields. More specifically, magnetic stereotactic systems have been developed that are particularly advantageous for positioning of catheters, as well as other devices, into areas of the body. The externally-generated magnetic fields and gradients are generated to precisely control the position of the catheter within the patient's body. Such stereotactic systems operate by monitoring the position of the catheter tip in response to the applied magnetic fields and, using well established feedback and control algorithms, controlling the fields so that the catheter tip is guided to and positioned in a desired location within the patient's body. Once positioned, physicians may operate the catheter, for example, to ablate tissue to interrupt potentially pathogenic heart rhythms or to clear a passage in the body.

However, the magnetic response of the catheter in such magnetic guidance systems can be a limitation on the precise control of a catheter. Improvements in catheters utilized with magnetic guidance and control systems, such as stereotactic systems, are desired. Specifically, a low cost, yet high performance magnetically guided catheter is desirable.

As further background, it is known generally that catheter ablation (e.g., RF ablation) may generate significant heat, which if not controlled can result in undesired or excessive tissue damage, such as steam pop, tissue charring, and the like. It is therefore common (and desirable) to include a mechanism to irrigate the target area and the device with biocompatible fluids, such as a saline solution. The use of irrigated ablation catheters can also prevent the formation of soft thrombus and/or blood coagulation. There are two general classes of irrigated electrode catheters, i.e., open irrigation catheters and closed irrigation catheters. Closed ablation catheters usually circulate a cooling fluid within the inner cavity of the electrode. Open ablation catheters typically deliver the cooling fluid through open outlets or openings on or about an outer surface of the electrode. Open ablation catheters often use the inner cavity of the electrode, or distal member, as a manifold to distribute saline solution, or other irrigation fluids, to one or more passageways that lead to openings/outlets provided on the surface of the electrode. The saline thus flows directly through the outlets of the passageways onto or about the distal electrode member.

One challenge in developing a magnetically-guided, open-irrigated ablation catheter, however, is how to deploy a tip positioning magnet so as to avoid contact with the irrigation fluid. This challenge stems from the fact that the magnetic material that would typically be used in the tip positioning magnet is highly susceptible to corrosion when exposed to irrigation fluid. It would therefore be desirable to provide a magnetically-guided catheter design that reduces or minimizes material corrosion.

There is therefore a need to minimize or eliminate one or more of the problems set forth above.

BRIEF SUMMARY OF THE INVENTION

One advantage of the methods and apparatus described, depicted and claimed herein, in embodiments suitable for use in magnetically-guided irrigated ablation catheters, involves configurations that prevent irrigation fluid (e.g., saline) from coming into contact with a positioning magnet, thus preventing corrosion while retaining all the features of an irrigated magnetic electrode for RF ablation. Another advantage, in embodiments suitable for use magnetically-guided electrode catheters, involves configurations that prevent bio-fluids from coming into contact with the positioning magnet, thus preventing corrosion.

An electrode assembly embodiment suitable for use in a magnetically-guided open-irrigation ablation catheter includes an body, a manifold and an outer capsule. The body has a proximal shank portion and a distal (enlarged) portion and includes a tip-positioning magnet. The manifold includes a distribution cavity configured to receive irrigation fluid and an irrigation passageway in fluid communication with the distribution cavity which has a distal exit port for delivery of irrigation fluid. The manifold is configured to isolate the body (i.e., the magnetic material) from the cavity and passageway, thus also isolating the body from contact with irrigation fluid. The outer capsule surrounds the magnetic body and comprises electrically conductive material, which may be selectively energized. When energized, the distal portion of the outer capsule acts as an ablation surface.

In an embodiment, the body may comprise conventional magnetic materials (e.g., ferromagnetic), rare-earth compositions (e.g., Neodymium Iron Boron—NdFeB) or an electromagnet. In another embodiment, the manifold may comprise a self-supporting tubular structure that is contained within the body. In a further embodiment, the manifold may comprise an isolation coating applied to the body. Since the body contains certain features, such as longitudinally-extending grooves, these same features remain after being coated. The outside surfaces of the coated features cooperate with the inside surfaces of the outer capsule to create the manifold. In a still further embodiment, the outer capsule comprises an electrically-conductive coating, which may include multiple layers. The coating isolates the body from external bio-fluids that may cause corrosion. In yet another embodiment, the outer capsule comprises an electrically-conductive casing, which may include a tip cap, shank cover and a washer configured to cooperatively seal together and comprising electrically-conductive material, such as platinum or platinum alloys.

In a still further embodiment, an electrode assembly is provided that is suitable for use in a magnetically-guided electrode catheter (e.g., mapping catheter). The assembly includes an body and an outer casing. The body has a proximal shank portion and a distal relatively enlarged portion wherein the body includes a tip-positioning magnet. The outer casing surrounds the body. The outer casing includes a cup-shaped tip cap configured to cover the distal portion of the body and a cylindrical-shaped shank cover configured to encase the shank portion of the body. The casing comprises electrically conductive material so as to allow electrical interaction with an external device (e.g., mapping apparatus). The electrode assembly, particularly the shank cover, is configured to receive the distal end portion of a catheter shaft. Methods of manufacture are also presented.

The foregoing and other aspects, features, details, utilities, and advantages of the present disclosure will be apparent from reading the following description and claims, and from reviewing the accompanying drawings.

BRIEF DESCRIPTION OF THE DRAWINGS

FIG. 2 is an enlarged side view of the distal tip assembly of the catheter of FIG. 1, having a tip electrode assembly and a ring electrode assembly.

FIG. 3 is an isometric view of a positioning magnet (i.e., body) incorporated into the tip electrode assembly of FIG. 2.

FIG. 13 is an exploded, isometric view of the electrode assembly of FIG. 11, showing an electrode base, an isolated manifold and an electrode tip.

FIG. 14 is an isometric view of the electrode tip of FIG. 13 taken from a proximal point of view.

FIG. 26 is a side view of a fourth electrode assembly embodiment suitable for use in a magnetically guided, irrigated ablation catheter, having a multi-segment tip positioning magnet.

FIG. 27 is an end view of the multi-segment magnet of FIG. 26.

DETAILED DESCRIPTION OF THE INVENTION

Figure 1:
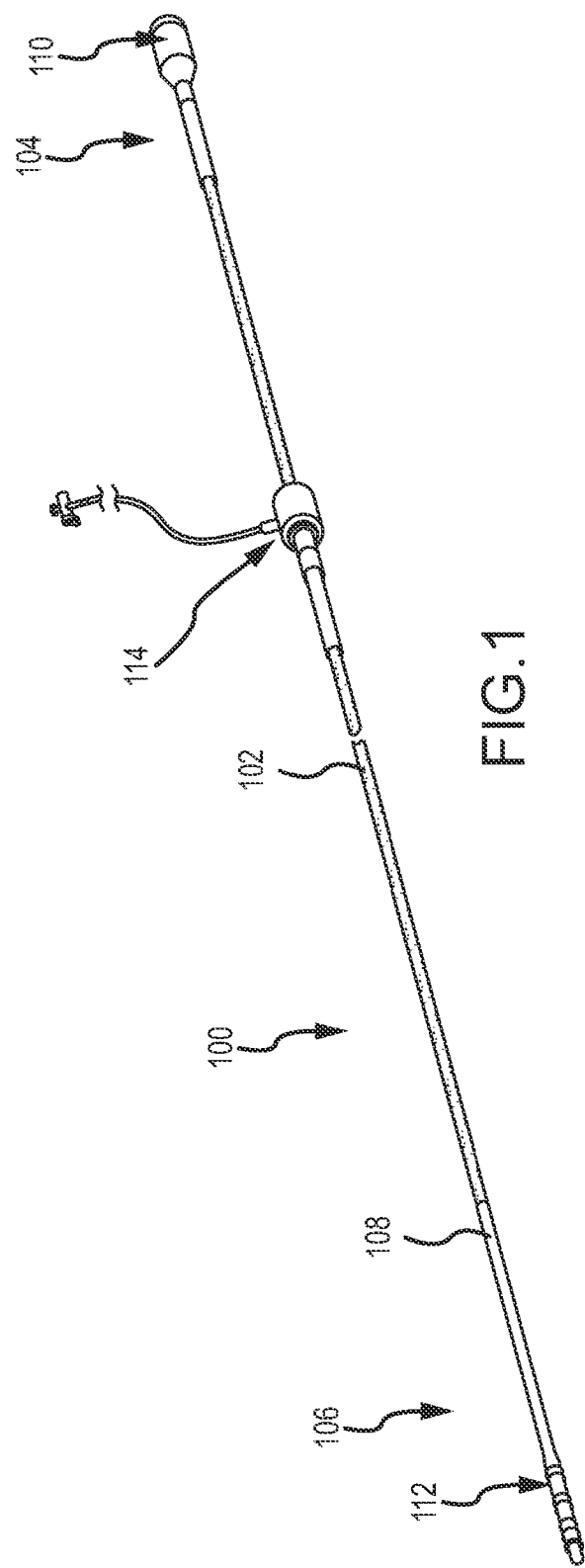
FIG. 1 is an isometric view of a first electrode assembly embodiment as used in a magnetically-guided catheter.

Referring now to the drawings wherein like reference numerals are used to identify identical components in the various views, FIGS. 1-10 show various aspects of a first electrode assembly embodiment. FIG. 1 in particular is a simplified, isometric view of a single-use magnetically guided catheter 100 that includes such an electrode assembly 112 at the distal end portion and operatively adapted for conducting a diagnostic or a therapeutic procedure under clinician control. In the illustrated embodiment, catheter 100 is a non-irrigated mapping catheter. Catheter 100 generally includes a flexible shaft in the form of an outer tube 102 having a proximal end portion 104, a distal end portion 106 and particularly including a relatively flexible segment 108. The soft segment 108 is configured so as to facilitate navigation of the catheter through the use of externally-applied magnetic fields interacting with a tip positioning magnet, as described in greater detail below. Of course, the segment 108 can be fabricated with a variety of different degrees of flexibility (e.g., analogous to a fishing pole having a graduated and increasing degree of flexibility from proximal to distal portions). Catheter 100 further includes an electrical connector 110 configured to establish electrical connection(s) between electrode portions of a catheter tip assembly 112 and external electrical apparatus (not shown) to perform, for example, mapping, ablation and/or pacing procedures, or to perform other aspects of a medical procedure. FIG. 1 further shows an introducer 114, in connection with which catheter 100 may be used.

Before proceeding to the detailed description, a brief overview of the contemplated use of the disclosed embodiments will first be set forth. The electrode assembly contained in catheter 100 (as well as the other electrode assembly embodiments described herein) is of the type that includes at least one positioning magnet in the tip assembly 112. The tip positioning magnet is configured to cooperate with externally-generated magnetic fields to provide for the guidance (i.e., movement) of the catheter tip to a desired location within the body. Thus, in operation, catheter 100, specifically tip assembly 112, may be navigated to a site in the body to perform a medical procedure, such as an atrial mapping, pacing and/or ablation. For example only, distal tip assembly 112 may extend into a heart chamber of a patient. Once the distal tip assembly 112 is disposed within the heart chamber, a magnetic field is applied which interacts with the tip positioning magnet, particularly the magnetic field produced by the tip magnet, to exert an orienting force on the tip assembly, allowing for precise positioning of the catheter tip assembly. The externally-generated magnetic fields used to orient the tip assembly 112 may be, in one embodiment, generated using a magnetic stereotactic system (not shown). Such stereotactic systems are known in the art and are commercially available from, for example only, Stereotaxis, Inc. of St. Louis, Mo. and Maple Grove, Minn. Such systems may include movable source magnets outside the body of the patient, and operative details of such systems are disclosed in, for example, U.S. Pat. Nos. 6,475,223 and 6,755,816, the disclosures of which are hereby incorporated by reference in their entirety. While catheter 100, as well as catheters employing other electrode assembly embodiments disclosed herein, may be advantageously used with a stereotactic system, the invention contemplates that magnetic fields and gradients to deflect the catheter tip assembly 112 may be alternatively generated by other systems and techniques.

With continued reference to FIG. 1, flexible tubing 102 may be fabricated according to known processes, such as multilayer processing including extrusion processes, mandrel-based processes and combinations thereof from any suitable tubing material known in the art of medical instruments, such as engineered nylon resins and plastics, including but not limited an elastomer commercially available under the trade designation PEBAX® from Arkema, Inc. of a suitable durometer, melting temperature and/or other characteristics. In this regard, in one embodiment, the soft segment 108 comprises material that provides greater flexibility than the proximal remainder portion of shaft 102. For example only, shaft 102 other than in soft segment 108 may comprise material having a 72D (durometer) hardness and include braided material for kink reduction. The soft segment 108 may be non-braided material and have a 25D, 35D or 40D hardness (i.e., more flexible). The soft segment 108 is configured to allow for improved magnetic guidance through the control of externally-applied magnetic fields, as described above. In other words, the soft segment 108 allows precise positioning of the tip without having to overcome stiffness in the shaft. In a further embodiment, shaft 102 may be about 52.525 inches (128 cm) in length with the soft segment being about 5.375 inches (13.7 cm) in length. In a still further embodiment, shaft 102 may be 5F (French) in size with a 7F flare at the distal end portion 106, which is configured for a press-fit connection with tip assembly 112. Of course, variations are possible.

Electrical connector 110 may comprise a known connector configured to engage the external electronics (not shown) with, for example, a plug-in connection. One suitable electrical connector is a 14 pin REDEL® plastic connector commercially available from LEMO of Rohnert Park, Calif., although other connectors from various manufacturers may likewise be utilized. Although not shown, such external electronics may comprise, in the case of a mapping catheter such as catheter 100, visualization, mapping and navigation components known in the art, including among others, for example, an EnSite Velocity™ system running a version of NavX™ software commercially available from St. Jude Medical, Inc., of St. Paul, Minn. and as also seen generally by reference to U.S. Pat. No. 7,263,397 entitled "METHOD AND APPARATUS FOR CATHETER NAVIGATION AND LOCATION AND MAPPING IN THE HEART" to Hauck et al., owned by the common assignee of the present invention, and hereby incorporated by reference in its entirety. Additionally, an electrophysiological (EP) monitor or display such as an electrogram signal display or other systems conventional in the art may also be coupled (directly or indirectly).

FIG. 2 is an enlarged, side view showing, in greater detail, tip assembly 112. The tip assembly 112 includes a tip electrode assembly 116, a ring electrode assembly 118 and a plurality of electrical conductors 120. The tip electrode assembly 116 includes a proximal passive portion 122 and a distal active portion 124. The outside diameter (OD) of the proximal passive portion 122 is configured for a press-fit coupling with the inside diameter (ID) of shaft wall 126. Accordingly, the proximal passive portion 122, after connection to shaft 102, does not present an electrically conductive surface, for example, for mapping, localization and the like. Conversely, the distal active portion 124 remains exposed even as incorporated into catheter 100, and is thus configured to present an electrically conductive surface, for example, for electrical interaction with tissue. In one embodiment, active portion 124 comprises for example a 7F (i.e., diameter), 4 mm (i.e., length) exposed tip, although variations are possible as one of ordinary skill in the art will appreciate.

The ring electrode assembly 118 includes a plurality of ring electrodes $128_{R-2}$, $128_{R-3}$ and $128_{R-4}$. Like the distal active portion 124, the ring electrodes $128_{R-2}$, $128_{R-3}$ and $128_{R-4}$ remain exposed even as incorporated into catheter 100 and thus present an electrically conductive surface, for example, for mapping, localization and the like. In one embodiment, inter-electrode spacing may be equal and may be approximately 2 mm. The tip electrode, active portion 124 and ring electrodes $128_{R-2}$, $128_{R-3}$ and $128_{R-4}$ are electrically coupled to electrical connector 110 by way of electrical conductors 120.

FIG. 3 is an isometric view of a magnet body 130 (also referred to herein as the tip positioning magnet) of tip electrode assembly 112. The body 130 is generally the innermost component of tip electrode assembly 116. The body 130 is generally cylindrical in shape, extending along an axis "A" and includes a proximal shank portion 132 having a first diameter 134 and a distal tip portion 136 having a second, larger diameter 138. Distal tip portion 136, while generally cylindrical, includes a generally hemispherical distal surface 140. The body 130 further includes a shoulder 142 at the transition between shank portion 132 and distal tip portion 134 and may further include a blind bore 144 (best shown in FIG. 7 as denoted by reference numeral 168 therein). In one embodiment, the body 130, after final magnetization (described below), produces a magnetic field oriented along axis A, having a north (N) pole (i.e., from which magnetic field lines extend) at the distal end portion and a south (S) pole (i.e., to which magnetic field lines terminate) at the proximal end portion.

In an embodiment, body 130 may be a permanent magnet fabricated from a known magnetic materials, such as ferromagnetic materials, or in alternative embodiments, fabricated from compositions including rare-earth materials, such as neodymium-iron boron-43 (NdFeB-43), neodymium-iron boron-45 (NdFeB-45), neodymium-iron boron-48 (NdFeB-48) or neodymium-iron boron-50 (NdFeB-50). Other magnet material compositions may be used; however, it should be appreciated that any particular selection of an alternate magnetic material composition will involve balancing of the resultant magnetic field strength of the tip positioning magnet versus the externally-generated magnet field strength developed by the external magnetic guidance systems (i.e., the resulting force developed on the catheter tip for guidance is a function of both magnetic field strength levels).

In an embodiment, body 130 is manufactured in a multi-step powdered metallurgical manufacturing process. First, the magnetic material (e.g., micron size Neodymium and iron boron powder) are produced in an inert gas atmosphere. Second, the magnetic material is pressed or compacted (i.e., compressed) in a mold, for example, in a brick or block shape and then the material is heated in a sintering step to render the material as a unitary structure. The result is a brick or block shaped slug. The magnetic performance may be optimized by applying a magnetic field either before, after, or during compaction (and/or sintering) wherein the applied field imparts a desired direction of magnetization or orientation in the NdFeB alloy magnet. The sintered slug may then be sub-divided into pieces. The individual pieces may thereafter be machined into their final form having the desired shape and dimensions using conventional approaches (e.g., diamond tooling for grinding, electrostatic discharge machining (EDM) or the like). Note, this machining step is preferably performed when the pieces are in an un-magnetized state.

Figure 25A:
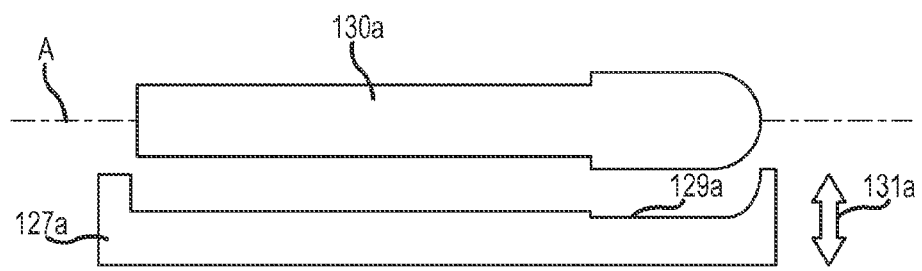
FIGS. 25A-B are side views of respective machining approaches for producing magnet pellets.
Figure 25B:
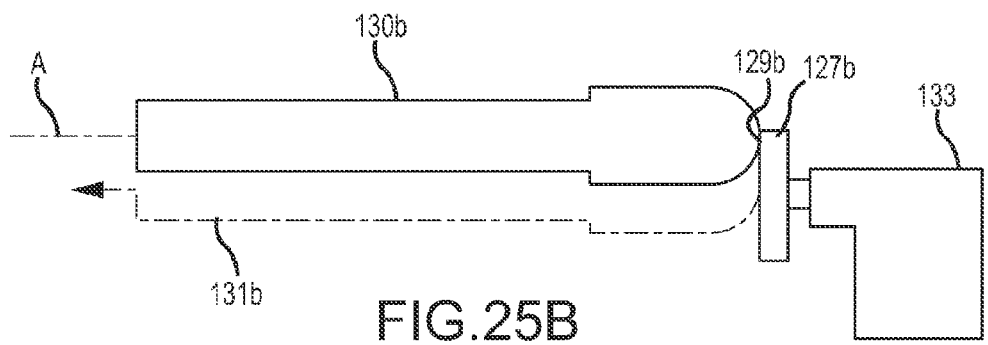

FIGS. 25A-B are simplified side views of multiple approaches for machining the sintered pieces. FIG. 25A shows a first embodiment that involves a fixture 127*a* configured with a cutting surface 129*a* (e.g., diamond tipped). The cutting surface 129*a* may correspond to the whole length of the machined piece 130*a*. The workpiece 130*a* is rotated about axis A, while relative movement is imparted between the fixture 127*a* and the workpiece 130*a* in a direction substantially normal to axis A so as to cut the workpiece 130*a* in the shape of (i.e., the profile of) the cutting surface 129*a*. In one embodiment, the fixture 127*a* is moved toward the workpiece in the direction 131*a* to commence machining and then moved away from the workpiece, also in direction 131*a*, when the cutting/machining operation has been completed. Of course, in the alternative, the workpiece 130*a* may be moved relative to the fixture 127*a*, or some combination of movements by each of the fixture and workpiece are possible.

FIG. 25B shows a second embodiment for machining a workpiece 130*b* that involves a cutting tip 127*b* having a cutting surface 129*b* configured for movement along a toolpath 131*b*. The cutting tip 127*b* may be a diamond-tipped cutting bit or the like and may be coupled to movement mechanism 133. In an embodiment, the mechanism 133 may be configured to both move (i.e., rotate) workpiece 130*b* about axis A as well as move (i.e., linear movement) the cutting tip 127*b* along the toolpath 131*b* (e.g., the mechanism 133 may be a lathe having a moveable tip position relative to axis A). In a further embodiment, the mechanism 133 may be a CNC lathe where the toolpath 131*b* may stored in a memory as data corresponding to the toolpath 131*b*. One advantage of the method of manufacture using the arrangement of FIG. 25B is the reduced cost of the cutting bit 127*b*, for example, as compared to the whole-length custom fixture 127*a* shown in FIG. 25A, with a custom configured surface 129*b*.

Finally, the machined pieces ("pellets") are subjected to a magnetic field sufficient to magnetize the pellets to saturation. In a still further embodiment, in the step above where the sintered slug is sub-divided, the method of manufacture preferably involves selecting those un-machined pieces from the center and discarding those sub-divided pieces from the end of the sintered slug. For example, where the sintered slug is a brick or block shaped slug, which is sub-divided into six un-machined pieces, the four center, and more preferably the two center un-machined pieces are selected for further processing while the end pieces are discarded. It is believed that the due to the manufacturing process involved, the center pieces will exhibit (after magnetization) greater magnetic (field) strength and uniformity for improved magnetic performance.

In still further alternative embodiments, body 130 may comprise an electro-magnet of conventional configuration that may be selectively energized and de-energized so as to produce and discontinue, respectively, production of a magnetic field. The electro-magnet embodiment may be, during a blanking interval, briefly de-energized from time to time so as to discontinue production of a magnetic field. The external magnetic field(s) used for guidance may also be discontinued in synchronism during the blanking interval. During such blanking interval, an imaging system that would otherwise experience interfering effects due to magnetic fields may be activated to acquire imaging data. Further during such blanking interval, an external localization system may be used to acquire localization information regarding catheter 100 (or other devices) without any of the interfering effects that may otherwise exist due to either the externally-generated magnetic fields or the magnetic field generated by the positioning magnet itself. Such external localization system may comprise conventional apparatus known generally in the art, for example, an EnSite Velocity system having NAVX™ software functionality, commercially available from St. Jude Medical, Inc. and as generally shown with reference to commonly assigned U.S. Pat. No. 7,263,397 titled "Method and Apparatus for Catheter Navigation and Location and Mapping in the Heart," the entire disclosure of which is incorporated herein by reference or other known technologies for locating/navigating a catheter in space (and for visualization), including for example, the CARTO visualization and location system of Biosense Webster, Inc., (e.g., as exemplified by U.S. Pat. No. 6,690,963 entitled "System for Determining the Location and Orientation of an Invasive Medical Instrument" hereby incorporated by reference), the AURORA® system of Northern Digital Inc., a magnetic localization system such as the gMPS system based on technology from MediGuide Ltd. of Haifa, Israel and now owned by St. Jude Medical, Inc. (e.g., as exemplified by U.S. Pat. Nos. 7,386,339, 7,197,354 and 6,233,476, all of which are hereby incorporated by reference) or a hybrid magnetic field-impedance based system, such as the CARTO 3 visualization and location system of Biosense Webster, Inc. (e.g., as exemplified by U.S. Pat. No. 7,536,218, hereby incorporated by reference). In this regard, some of the localization, navigation and/or visualization systems may involve providing a sensor for producing signals indicative of catheter location information, and may include, for example one or more electrodes in the case of an impedance-based localization system such as the EnSite™ Velocity system running NavX software, which electrodes already exist in the case of catheter 100, or alternatively, one or more coils (i.e., wire windings) configured to detect one or more characteristics of a low-strength magnetic field, for example, in the case of a magnetic-field based localization system such as the gMPS system using technology from MediGuide Ltd.

Figure 4:
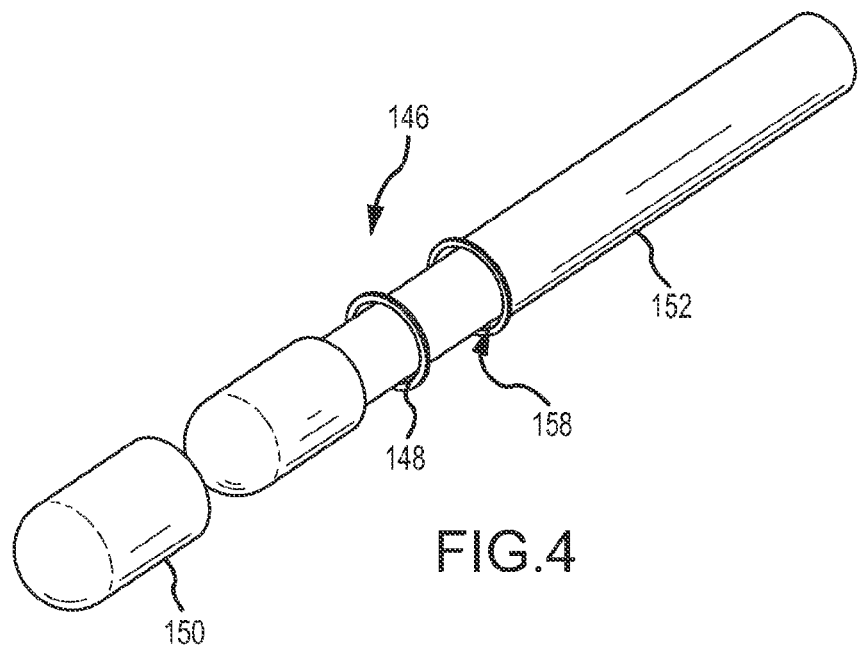
FIGS. 4-5 are isometric views showing an intermediate stage of manufacture where a tip cap, ring and shank cover are assembled over and onto the tip positioning magnet of FIG. 3.
Figure 5:
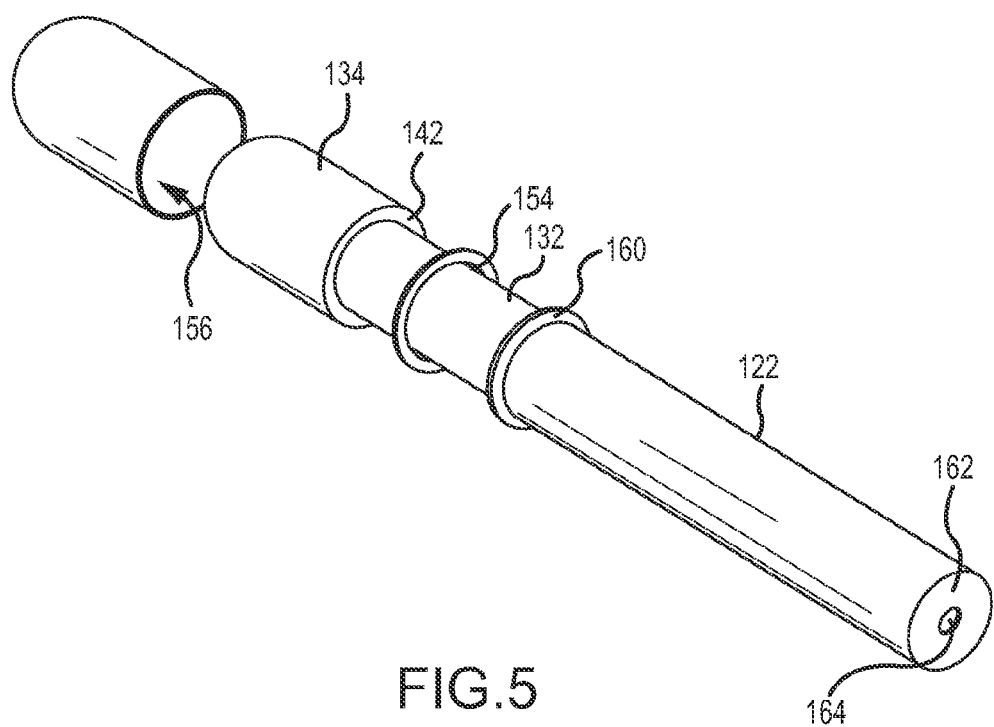

FIG. 4-5 are isometric views showing a sub-assembly of tip electrode assembly in an intermediate stage in the manufacture. In particular, tip electrode assembly 116 includes an electrically-conductive capsule in the form of an outer casing 146 overlying and surrounding body 130 (i.e., overlying and surrounding the positioning magnet). The casing 146 is configured to provide corrosion resistance for the underlying body 130, which is susceptible to corrosion, in addition to providing excellent electrical conducting characteristics. The casing 146 includes a washer (or ring) 148, a tip cap 150 and a shank cover 152.

The washer 148 includes a hole 154 and the tip cap 150 includes an opening 156. The shank cover 152, as shown, includes an opening 158, a flange 160 and a floor wall 162 having an aperture 164. In an embodiment, the components 148, 150, 152 may comprise a biocompatible metal, such as platinum (e.g., 99.95% Pt) or its alloys (i.e., 90% Platinum (Pt):10% Iridium (Ir)) and may have a predetermined, desired thickness (e.g., 0.002"). In an embodiment, the metal for the components of casing 146 preferably has a relatively fine grain (e.g., preferably having a grain size of 4 or larger, more preferably having a grain size of 6 or larger). Of course, variations are possible. Examples of other suitable electrically conductive materials also include (but are not limited to) gold, platinum, iridium, palladium, copper, nickel, stainless steel, and various mixtures, alloys and combinations thereof. In other variations, the electrically-conductive material may be applied to the outer surface of the body 130 by known methods, such as by chemical vapor deposition (CVD), sputtering, mechanical 'spinning' with a mold and a tool to press sheet-form materials to the mold, plating, painting and the like.

With regard to the manufacture of the components of casing 146, washer 148 may be manufactured using sheet stock of the raw material through conventional stamping and/or cutting (e.g., laser cutting) operations. The tip cap 150 may be manufactured using a progressive, draw process, in which a blank (i.e., the raw material, which may be a 0.002" thick sheet material in the shape of a circle in one embodiment) is fed through a series of dies, each progressively smaller in diameter, until the desired, final tip cap shape and dimension is achieved. Likewise, the shank cover 152 may be manufactured using a progressive, deep draw process, in which a blank is fed through a series of dies, each progressively smaller, until the final shape and dimension is achieved. In the case of shank cover 152, additional operations are also required such as creating flange 160 at the open end thereof and creating aperture 164 through floor 162. As to the latter operation, a laser or stamping operation may be used. It should be understood that variations are possible for producing the components of casing 146 (e.g., hydroforming may be used as an alternative to a deep drawing operation).

With continued reference to FIGS. 4-5, assembly of the casing 146 to surround body 130 involves first placing the washer 148 over the shank portion 132 through washer hole 154 and seating the washer 148 against shoulder 142. Next, the tip cap 150 is placed on the body 130 by orienting the opening 156 of the tip cap 150 toward the distal portion 134 and then inserting until the tip cap is fully seated. The shank cover 152 is likewise placed on the body 130 by orienting the opening 158 toward the proximal end portion of the body shank and then inserting until the flange 160 is seated against the washer 148, which is itself seated against shoulder 142.

Figure 6:
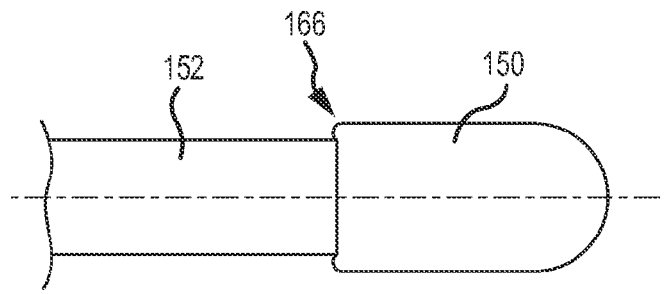
FIG. 6 is a side view of the tip electrode assembly of FIG. 2.

Turning now to FIG. 6, the next step results in creating a seal at the junction or joint 166. The proximal edge of the tip cap 150 may be rolled or crimped (as shown at junction or joint 166) over the flange 160 and washer 148, and then welded, for example, by laser welding. In this regard, the washer 148 is particularly useful where the transition is laser welded since the washer 148 protects the underlying magnet body from the laser beam as well as provides material that is liquefied to become part of the weld "puddle", thereby improving the resultant bond and seal. The casing 146 may now be considered unitary and except for aperture 164, which will be sealed as described below, provides isolation for body 130 and thus protects body 130 against corrosion.

Figure 7:
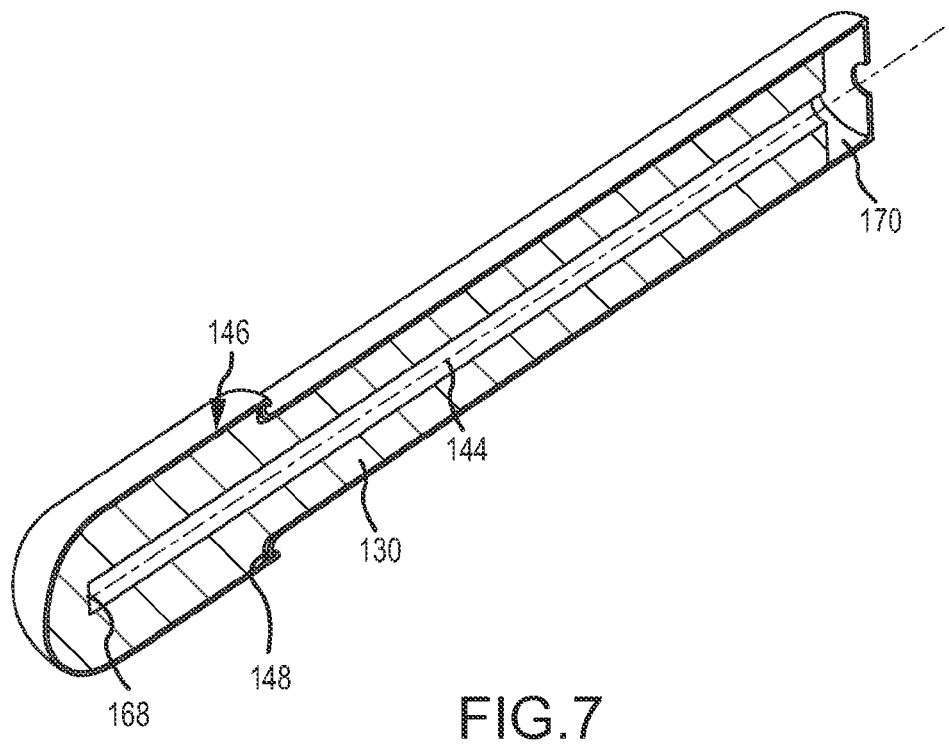
FIG. 7 is a cross-sectional view of the tip electrode assembly of FIG. 2.

FIG. 7 is a cross-sectional view of tip electrode assembly 116. As shown, blind bore 144 include a floor 168. In the illustrative embodiment, the proximal shank portion 132 of body 130 may be axially shorter than an inner length of the shank cover 152, thereby creating a chamber 170. The extra space afforded by chamber 170 may be useful in easing assembly of the shank cover to the shank portion of the magnet body (i.e., reduces or eliminates dimensional interference between the proximal end of the magnet body and the inside surface of the floor of the shank cover).

Figure 8:
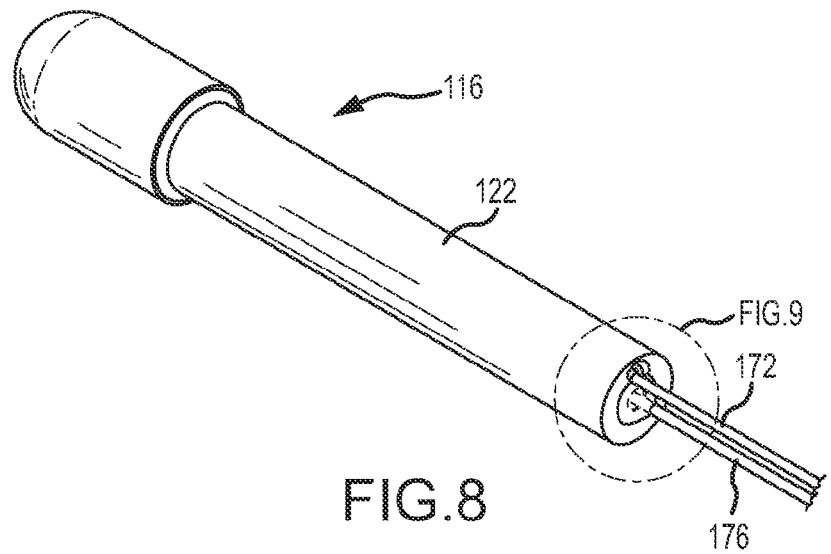
FIG. 8 is an isometric view of the tip electrode assembly of FIG. 2 showing an electrical connection and a safety line.
Figure 9:
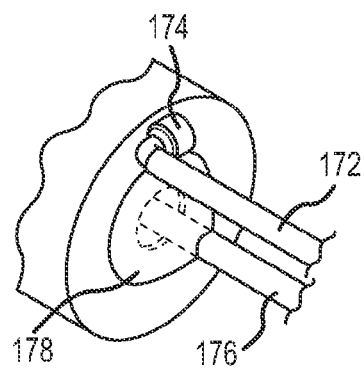
FIG. 9 is an enlarged isometric view of the encircled region of FIG. 8.
Figure 10:
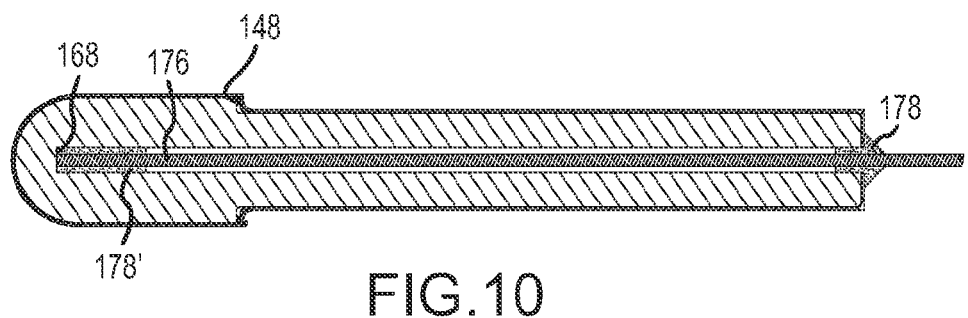
FIG. 10 is cross-sectional view of the tip electrode assembly of FIG. 2 including connections.

FIGS. 8-9 are isometric views of tip electrode assembly 116, particularly the proximal end portion thereof. To provide electrical connectivity, an electrical conductor 172 is electrically connected to conductive casing 146 at point 174 (e.g., soldered connection to the shank cover 152 on exterior of the floor wall 162). The proximal end portion of conductor 172 extends toward and terminates at electrical connector 110. Conductor 172 may comprise conventional materials and approaches (e.g., 34 AWG wire, insulated, solderable). As described above, the connector is, in turn, connected to various external apparatus.

FIG. 9 further shows a safety line 176. The line 176 is configured to restrain and/or limit stretching of the distal assembly 112 (i.e., the soft segment 108 of shaft 102) that may otherwise occur through repeated advance/retract cycles of catheter 100. The line 176 also provides additional assurance that tip electrode assembly 116 will not disconnect from the catheter (i.e., from the shaft 102). In an exemplary embodiment, a high tensile strength LCP (liquid crystal polymer) fiber wire may be used as line 176, or alternatively, line 176 may comprise a high strength fibrous material, for example, a para-aramid synthetic fiber commercially available under the trademark KEVLAR® from E.I. du Pont de Nemours and Company, Wilmington, Del., U.S.A. One end of line 176 may be affixed or anchored at connector 110 or alternatively wound around the shaft at the proximal hub. The line 176 is also affixed at the distal end portion specifically to tip electrode assembly 116. In an exemplary embodiment, line 176 is affixed to body 130 by tying a knot (not shown) at one end of line 176 and then press-fitting the knotted end through aperture 164 and into the blind bore 144 until seated on floor 168. An adhesive (e.g., LOCTITE® 4981 or the like) is then applied to bond the knot at the floor 168, as shown more particularly in FIG. 10 as adhesive 178. The adhesive is then allowed to cure. The aperture 164 may then be sealed by the use of a suitable adhesive/sealant, such as adhesive 178, thereby completely sealing the body 130 from potential sources of corrosion. Adhesive 178 and adhesive 178' may be the same adhesive.

Figure 11:
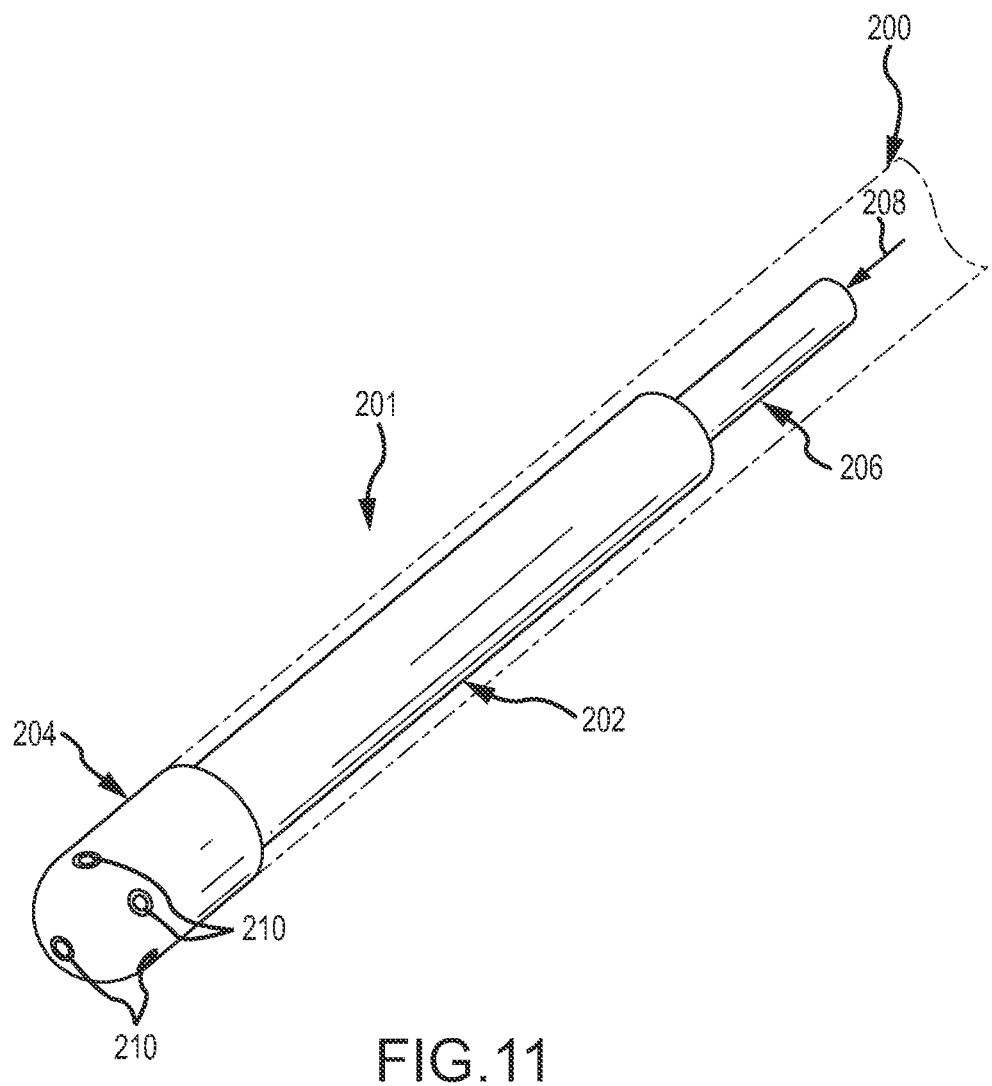
FIG. 11 is an isometric view of a second electrode assembly embodiment suitable for use in a magnetically-guided, irrigated ablation catheter.

FIGS. 11-18 are directed to a second electrode assembly embodiment and FIG. 11 in particular is an isometric view of a single-use magnetically-guided, open-irrigation radio-frequency (RF) ablation catheter 200. Of course, other forms or sources of energy can be utilized in conjunction with the inventive catheters hereof, including microwave, cryogenic, optical and the like. Catheter 200 includes a tip electrode assembly 201 that includes a tip positioning magnet. A shaft of catheter 200 is shown in phantom-line and the proximal portion of the catheter 200 (e.g., the proximal hub, etc.) has been omitted for clarity, although it should be understood that generally conventional catheter structures (e.g., shaft, handle, irrigation tube, etc.) may be used in connection with tip electrode assembly 201, with the exception that the distal shaft section of catheter 200 may also comprise a soft segment, like soft segment 108 described above in connection with catheter 100. Further, it should be understood that embodiments of catheter 200 may, and typically will, include additional structural and functional features that have been omitted for clarity (e.g., irrigation tube, temperature sensor and associated connecting wires, etc.).

The tip electrode assembly 201 includes a proximal passive portion 202 having a first diameter that is reduced as compared to a second diameter of a distal active portion 204. The passive proximal portion is covered by the catheter shaft and thus has no exposed, electrically-conductive surfaces. The active distal portion remains exposed in the final assembly (i.e., in catheter 200) and thus has an exposed electrically-conductive surface for interaction with tissue, such as for RF ablation. As described in the Background, the magnetic material used for the tip positioning magnet may be susceptible to corrosion if contacted with irrigation fluid or body fluids. To achieve the desired isolation from irrigation fluid, tip electrode assembly 201 includes an irrigation fluid manifold 206 into which irrigation fluid 208 (e.g., saline solution) flows, which is destined for delivery via a plurality of exit irrigation ports 210.

Figure 12:
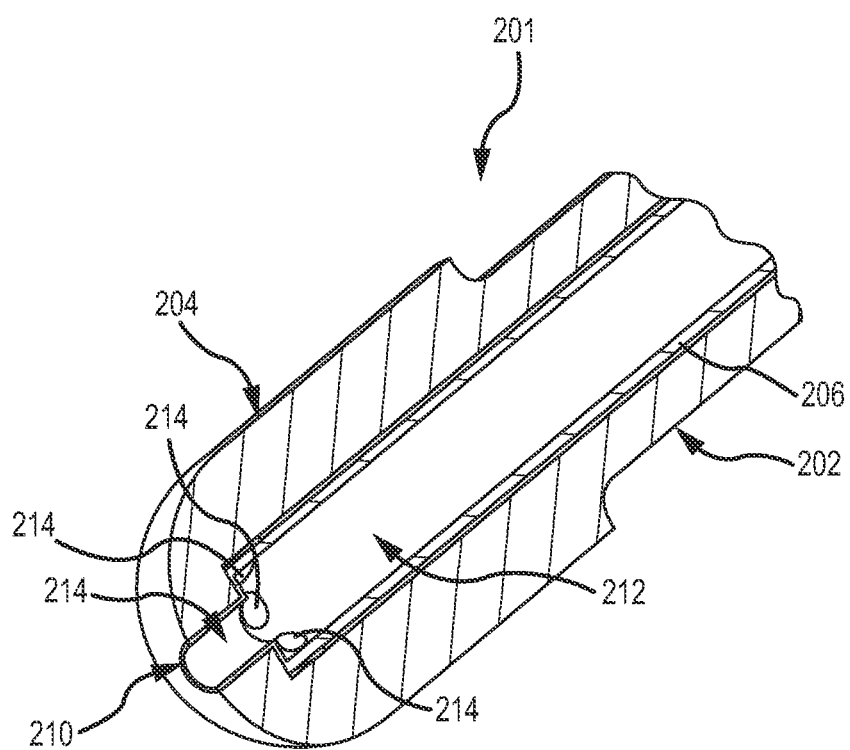
FIG. 12 is cross-sectional view of the electrode assembly of FIG. 11.

FIG. 12 is a cross-sectional view of tip electrode assembly 201. As shown, the manifold 206 includes a distribution cavity 212 in fluid communication with a plurality of irrigation passageways 214. The manifold 206 is configured to isolate the irrigation fluid from coming into contact with the positioning magnet and can be lined or coated (e.g., with non-permeable material, insulation, or the like).

FIG. 13 is an exploded, isometric view of tip electrode assembly 201 in a preliminary stage of manufacture. The tip electrode assembly 201 includes a main magnet body 216, which in turn includes an electrode base 218 and an electrode tip 220 that together the tip positioning magnet.

Electrode base 218 and electrode tip 220 may comprise the same magnetic material or electro-magnetic configuration as described above in connection with body 130. Further, electrode base 218 and electrode tip 220 may also be manufactured using the same or substantially similar method steps described above in connection with body 130 (i.e., compaction, sintering, machining and magnetizing), with the exception that the machining step will be somewhat different as to shape, features and dimensions, as described further below.

As shown, electrode base 218 is generally cylindrical and includes an axially-extending central lumen 222 having openings on both axial ends thereof, a reduced diameter shank portion 224, an increased diameter distal portion 226 (i.e., an increased diameter relative to the diameter of shank portion 224), a shoulder 228 at the transition between portions 224 and 226 and a plurality of radially-distributed half-channels 230. The half-channels 230 have respective axes that are substantially normal to the main axis "A" of base 218.

The electrode tip 220 includes an outer distal surface 232 that establishes the shape for an active ablation surface, a plurality of radially-distributed half-channels 234 that correspond to half-channels 230 and an axially-arranged bore 236 that extends through electrode tip 220. In one embodiment, the distal tip may be rounded (e.g., partially spherical or hemispherical), although other configurations may be used.

FIG. 14 is an isometric view of electrode tip 220 showing radially-distributed half-channels 234. Like the half-channels 230, half-channels 234 have axes that are substantially normal to the main axis "A" (when assembled).

The isolated manifold 206, in one embodiment, may comprise polyimide material, although it should be understood that variations in material choice are possible. Generally, manifold 206 comprises material that will isolate irrigation fluid from contact with the underlying body 216 so as to inhibit or suppress the corrosive effects that irrigation fluid may otherwise have on the magnetic material. Manifold 206 may comprise thermally nonconductive or reduced (i.e. poor) thermally conductive material that serves to insulate the fluid from the remaining portions of the electrode assembly. Moreover, material(s) for manifold 206 may also exhibit electrically nonconductive properties. Examples of suitable materials include, but are not limited to, polyether ether ketone ("PEEK"), high-density polyethylene, polyimides, polyaryletherketones, polyetheretherketones, polyurethane, polypropylene, oriented polypropylene, polyethylene, crystallized polyethylene terephthalate, polyethylene terephthalate, polyester, polyetherimide, acetyl, ceramics, and various combinations thereof.

Manifold 206 includes a longitudinally-extending tubular portion 238 having a cavity 212 (best shown in FIG. 12), a fluid inlet 240, and a generally radially-distributed distal portion 242. The radially-distributed distal portion 242 includes a plurality of tubes 244 which include a corresponding plurality of irrigation passageways 214 (best shown in FIG. 12). In one embodiment, manifold 206 is of thin-wall construction (e.g., 0.002" wall thickness) although it is relatively rigid and thus self-supporting.

Figure 15:
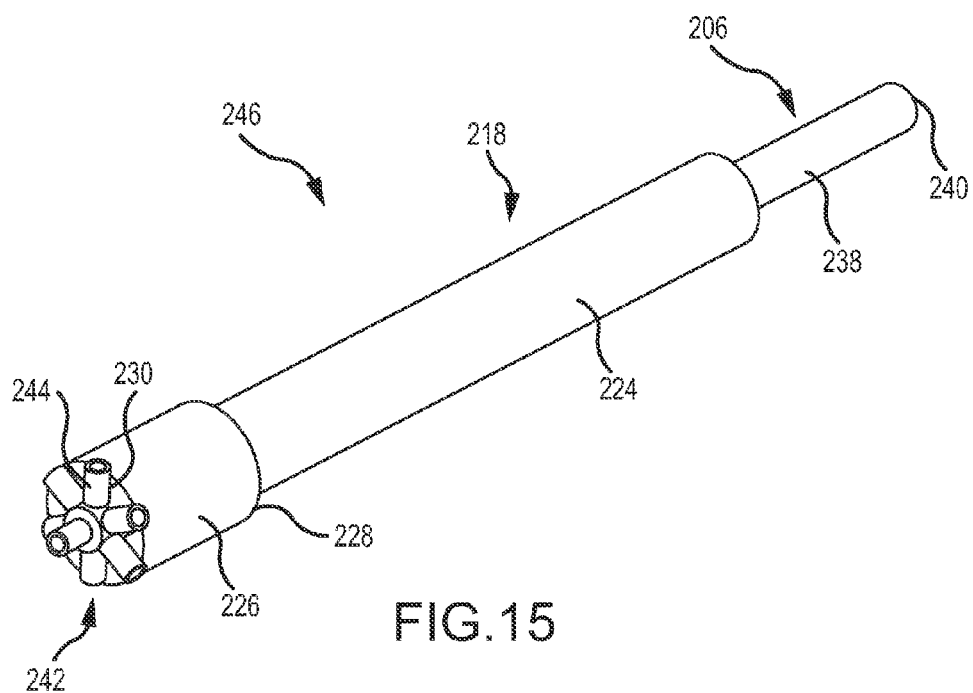
FIG. 15 is an isometric view showing a sub-assembly of the electrode assembly of FIG. 11 in a first stage of manufacture.

FIG. 15 is an isometric view of a first sub-assembly 246 of tip electrode assembly 201 in a first stage of manufacture. An overall method of manufacture of electrode assembly 201 includes a number of steps. The first step involves applying a bonding material, such as epoxy, onto the outer surface of manifold 206. The epoxy may comprise biocompatible, medical grade adhesive material(s). Second, inserting the proximal end portion of manifold 206 (i.e., opening 240 as shown in FIG. 13) into the distal end portion of electrode base 218 and then sliding the tubular portion 238 through lumen 222 until the radially-distributed tubes 244 are aligned with and are firmly seated in corresponding half-channels 230. The third step involves applying a bonding material, such as an electrically-conductive epoxy, on the distal, transverse outer surface of the electrode base 218 (best shown as epoxy layer 250 in FIG. 17). Fourth, attaching electrode tip 220 to the electrode base 218 such that (i) the axially-oriented tube 244 (i.e., extending along the main axis) is inserted into axial bore 236 and the exposed portions of the remaining radially-oriented tubes 244 are aligned with and seated in corresponding half-channels 234, thereby encasing the manifold 206 within the body.

Figure 16:
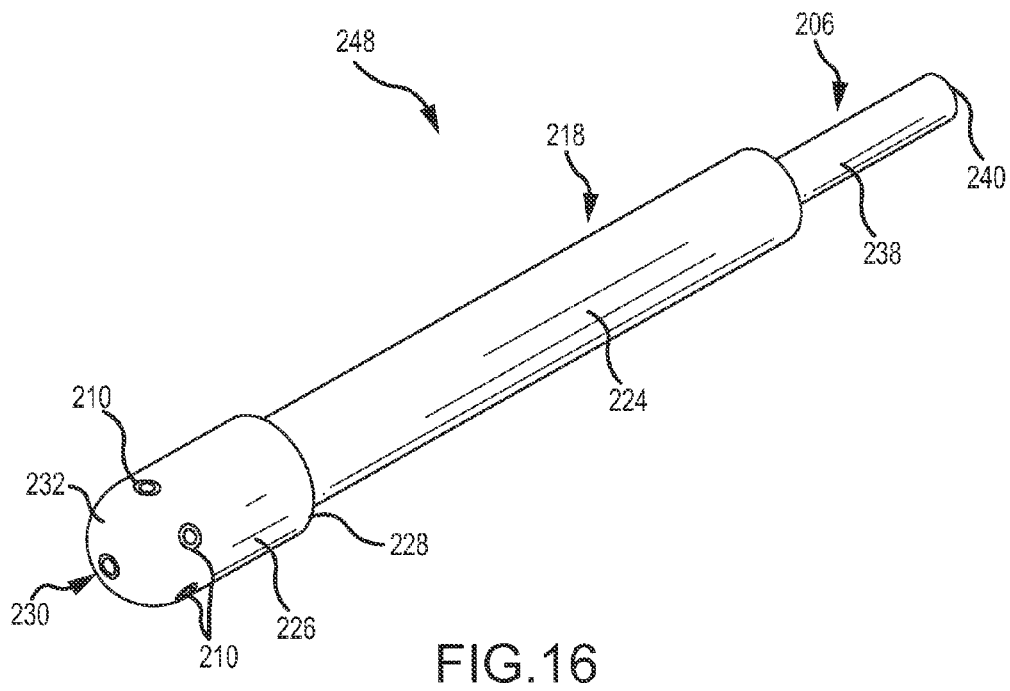
FIG. 16 is an isometric view showing a sub-assembly of the electrode assembly of FIG. 11 in a second stage of manufacture.

FIG. 16 is an isometric view of a further sub-assembly 248 of tip electrode assembly 201, in a further stage of manufacture. After electrode tip 220 has been attached, the next step in the method of manufacture involves applying an outer capsule, such as corrosion inhibiting coating 252 (best show in FIG. 17) to surround the body to isolate the body from bio-fluids to thereby inhibit or suppress corrosion.

Figure 17:
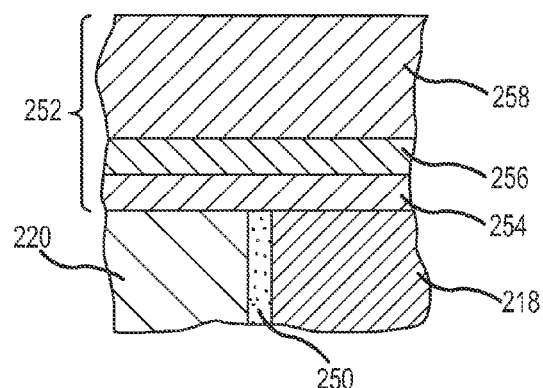
FIG. 17 is an exaggerated cross-sectional view of an electrically-conductive coating suitable for encapsulating the sub-assembly of FIG. 16.

FIG. 17 is an exaggerated, simplified cross-sectional view of a corrosion inhibiting coating 252 for encapsulating the sub-assembly 248 of FIG. 16. As described above, electrode base 218 and electrode tip 220 are coupled together by a layer of epoxy 250. This is shown in FIG. 17. Coating 252 also functions to bridge the discontinuity between tip 220 and base 218 due to the epoxy layer 250. Preferably, the epoxy is an electrically-conductive epoxy, although as will become apparent, this characteristic is not indispensable inasmuch as the outer, exposed layer of coating 252 is also electrically conductive. Coating 252 is thus configured to be relatively chemically impervious to the extent of bio-fluids, minimizing or eliminating migration of such fluids into contact with the body. Additionally, coating 252 is electrically-conductive, suitable for ablation, such as RF ablation. In the illustrated embodiment, coating 252 includes a first layer 254, a second layer 256 and a third layer 258.

In a first embodiment of coating 252, the first layer 254 may comprise Ni—Ni plating (e.g., approximately 2 mils (~50 microns) thick), with the a first sub-layer being electroless nickel (i.e., without the use of an electric current as typically used in electro-plating) and a second sub-layer comprising conventional nickel plating (e.g., by electroplating). Other conventional preparation steps, for example, surface cleaning steps (e.g., via use of an acid) and/or inter-layer surface preparation steps, may also be performed as understood by one of ordinary skill in the art. The second layer 256 may comprise gold (Au) material (e.g., approximately 2 microns thick) while the third layer 258 may comprise platinum (Pt) material (e.g., approximately 1 mil (~25 microns) thick).

In a second embodiment, the first layer 254 may also comprise Ni—Ni plating (e.g., approximately 2 mils (~50 microns) thick), the second layer 256 may comprise titanium (Ti) material (e.g., as by dc sputtering, approximately 20,000 Å thick) while the third layer 258 may comprise platinum (Pt) material (e.g., approximately 10,000 Å thick).

In both embodiments, the layers 254, 256 and 258 cooperate to form a multi-layer bonded surface/seal. In addition, in some embodiments, an additional nickel (Ni) "strike" (e.g., 1 Angstrom) may be applied on top of the Ni—Ni layer 254 to reactivate the nickel. This nickel strike may be desirable when some time has passed after the Ni—Ni layer has been applied before the second layer 256 is to be applied.

A further step, for example in a method for manufacturing catheter 200, involves making the necessary electrical and irrigation fluid supply connections between the electrode assembly and the catheter shaft and then embedding the proximal passive portion of tip electrode assembly 201 into the inside diameter portion of the shaft of catheter 200 (best shown in FIG. 11).

Figure 18:
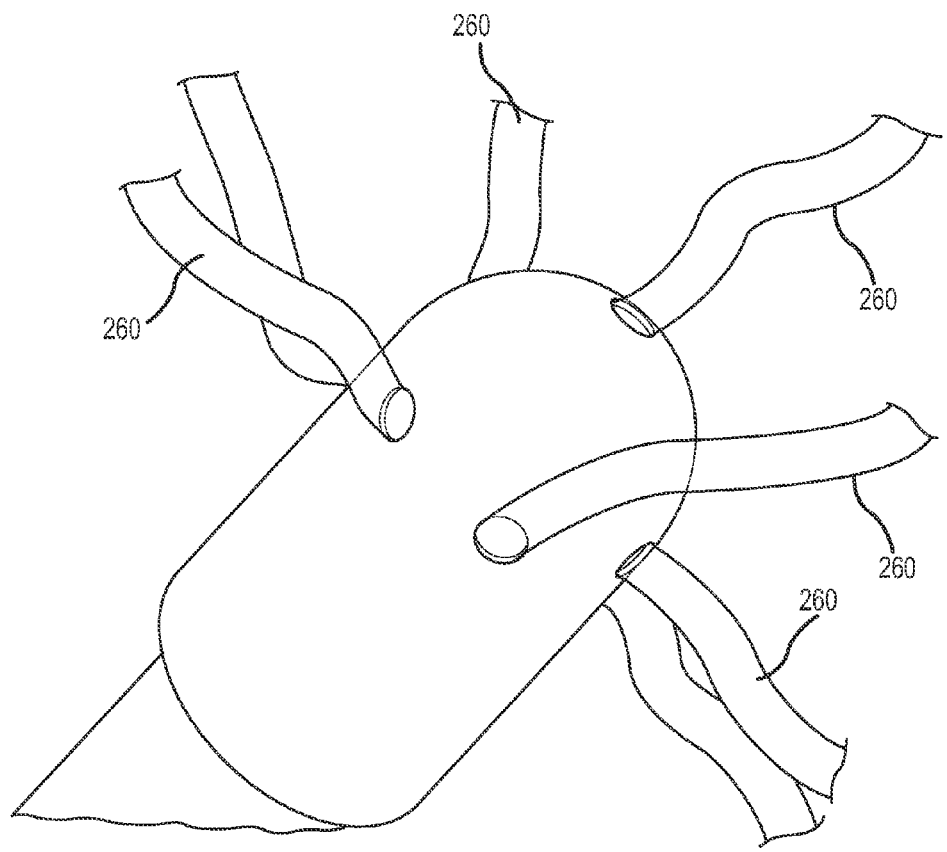
FIG. 18 is an isometric view of the electrode assembly of FIG. 16 showing the un-trimmed tail ends of a plurality of irrigation tubes.

FIG. 18 is an isometric view of tip electrode assembly 201 showing untrimmed tail ends 260 of irrigation tubes 244. In an alternate embodiment for manufacturing tip electrode assembly 201, tubes 244 may be kept longer than ultimately necessary for the final assembly (i.e., extending beyond the surface of the electrode) so as to prevent blockage of the irrigation ports. In this alternate embodiment, the additional length of the tubes 244 may preferably be trimmed flush with the tip surface.

Figure 19:
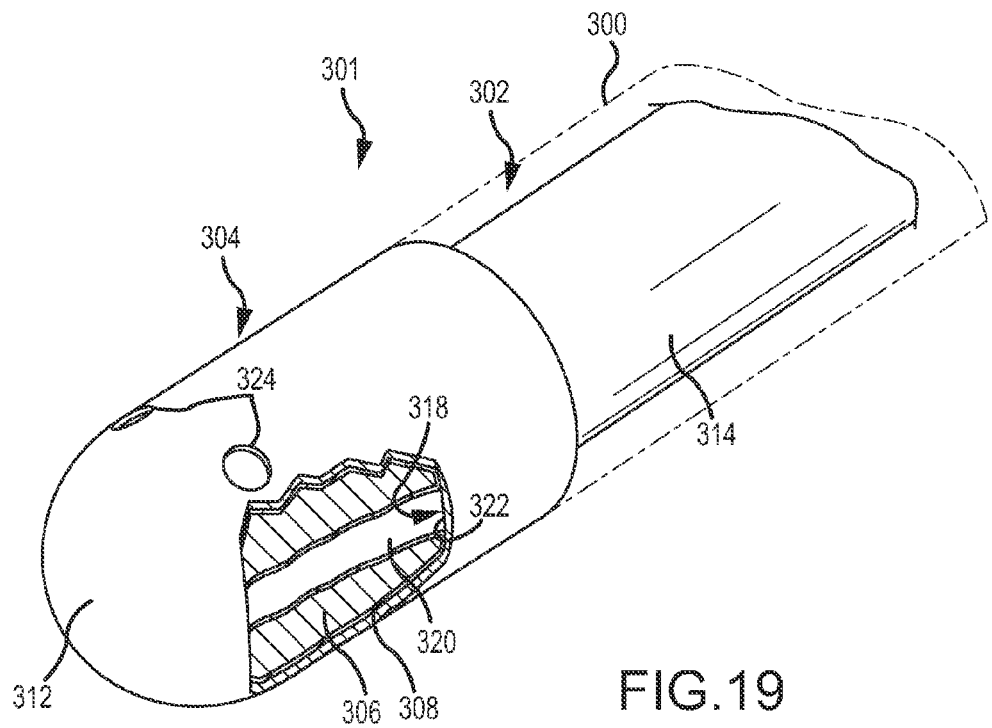
FIG. 19 is an isometric view of a third electrode assembly embodiment, shown partially in cross-section, suitable for use in a magnetically guided, irrigated ablation catheter.

FIGS. 19-24 are directed to a third electrode assembly embodiment and FIG. 19 in particular is an isometric view of a single-use magnetically-guided, open-irrigation RF ablation catheter 300 having such an electrode assembly (i.e., tip electrode assembly 301). The distal portion of a shaft of catheter 300 is shown in phantom while the proximal portion of catheter 300 (e.g., the proximal hub, etc.) has been omitted for clarity, although it should be understood that generally conventional catheter structures (e.g., shaft, handle, irrigation tube, etc.) may be used in connection with tip electrode assembly 301, with the exception that the distal shaft section of catheter 300 may also comprise a relatively flexible segment, like segment 108 described above in connection with catheter 100. Further, it should be understood that embodiments of catheter 300 may, and typically will, include additional structural and functional features that have been omitted for clarity (e.g., irrigation fluid feed tube, temperature sensor(s) and associated connecting wires, etc.).

The tip electrode assembly 301 includes a proximal passive portion 302 having a first diameter that is reduced as compared to a second diameter of a distal active portion 304. The passive proximal portion is covered by the catheter shaft and thus has no exposed, electrically-conductive surfaces. The active distal portion remains exposed in the final assembly (i.e., in catheter 300) and thus has an exposed electrically-conductive surface for interaction with tissue, such as for RF ablation. The constituent components of tip electrode assembly 301, from radially innermost to radially outermost, include a tip positioning magnet body 306, an isolated manifold 308 and an electrically-conductive capsule in the form of a casing 310 that surrounds the manifold 308. The casing 310 includes a tip cap 312, a shank cover 314 and a washer 316 (best shown in FIG. 23). Irrigation passageways 318 in electrode assembly 301 are created between an outside surface of a plurality of longitudinally-extending grooves 320 and the inside diameter (ID) of casing 310 (both the tip cap 312 and shank cover 314). The irrigation passageways 318 lead to a plurality of exit ports. In this regard, the tip cap 312 includes a plurality of apertures 324 that include such irrigation exit ports. The casing 310 (including constituent components 312, 314 and 316) may comprise the same materials as casing 146 described above for tip electrode assembly 116. Additionally, the components of casing 310 may be fabricated using the same methods described above in connection with the components of casing 146.

Figure 20:
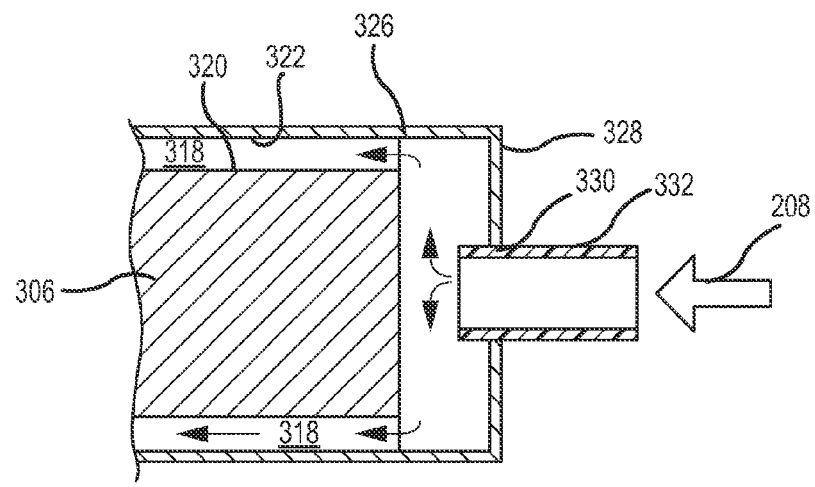
FIG. 20 is a partial cross-sectional view of the proximal end portion of the electrode assembly of FIG. 19, showing irrigation fluid flow paths isolated from the magnetic body.

FIG. 20 is a partial cross-sectional view of the proximal end portion of tip electrode assembly 301. The shank cover 314 includes a cylindrical outer wall 326 that extends into a base wall 328. Wall 328 includes an aperture 330. An irrigation fluid tube 332 is shown disposed in aperture 330 and into which irrigation fluid 208 flows. As described in the Background, the magnetic material used for body 306 may be susceptible to corrosion. Accordingly, tip electrode assembly 301 also includes manifold 308 through which irrigation fluid 208 flows destined for delivery via ports 324. FIG. 20 better shows how the irrigation passageways 318 are created between the outside diameter (OD) surface 320 of the manifold and the inside diameter (ID) surface 322 of wall 326. FIG. 20 further shows how manifold 308 isolates the irrigation fluid from contact with the positioning magnet, thereby preventing the above-mentioned corrosion.

As further shown in FIG. 20, tip electrode assembly 301 includes a distribution cavity generally at the outlet of irrigation tube 332, which feeds fluid to irrigation passageways 318. The distribution cavity is bounded generally by base wall 328, the proximal-most portion of sidewall 326 adjacent to base wall 328 and the proximal-most end surface of the coated body 306.

Figure 21:
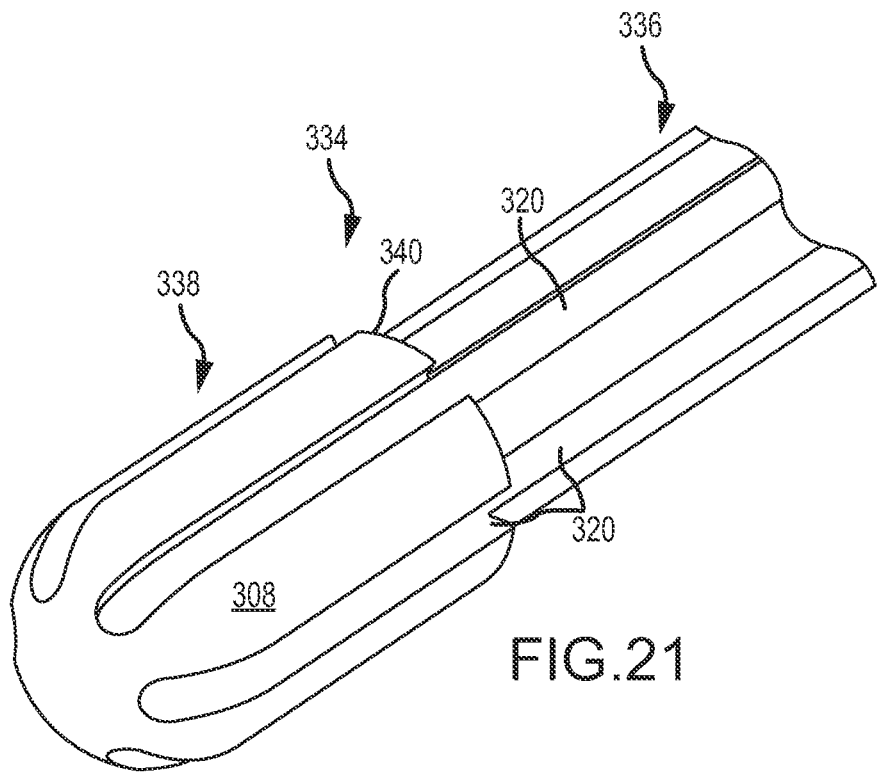
FIG. 21 is an isometric view of a sub-assembly of FIG. 19 in a first stage of manufacture.
Figure 22:
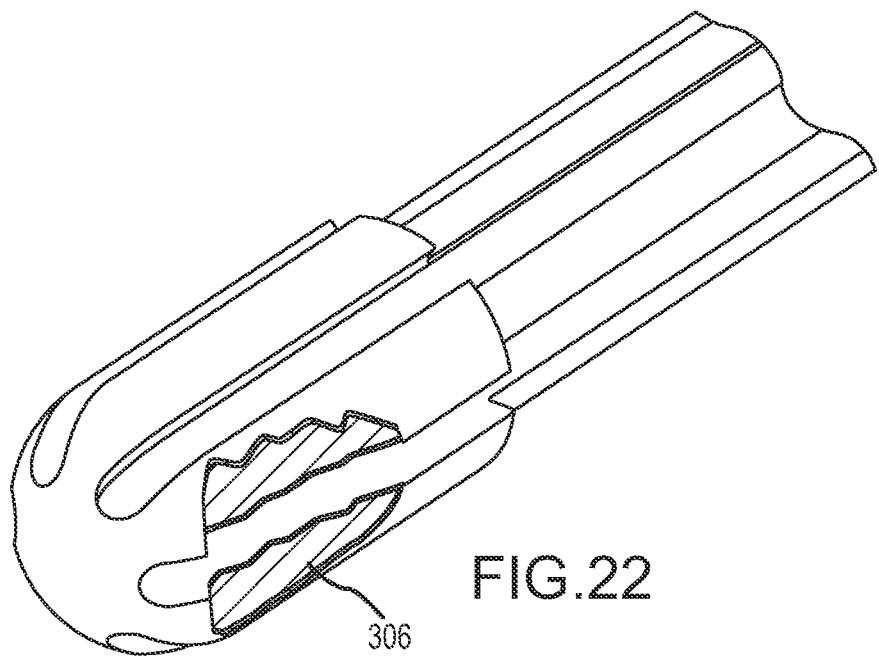
FIG. 22 is an isometric view of the sub-assembly of FIG. 19, shown partially in cross-section.

FIGS. 21-22 are isometric views showing a sub-assembly of tip electrode assembly 301 in an initial stage of manufacture. A method of manufacture includes a number of steps. The first step involves producing body 306, and in this regard body 306 may comprise the same magnetic materials or electro-magnetic configuration as described above in connection with body 130. Further, body 306 may be manufactured using the same or substantially similar method steps described above in connection with body 130 (i.e., compaction, sintering, machining and magnetizing), with the exception that the machining step will be somewhat different, with different shapes, features and dimensions, as described further below.

The next step involves applying an isolation layer to body 306 to thereby surround the body and establish one part of the isolated manifold 308. The isolation layer may comprise the same material as described for manifold 206, and in one embodiment, comprises a polyimide coating. As shown, the sub-assembly 334 includes a shank portion 336, a tip portion 338 and shoulder portion 340 located where the shank portion 336 and the tip portion 338 meet. It should be understood that body 306 is in substantially the same shape as shown in FIGS. 21-22 (which include the isolation layer) and thus includes all the same features. Accordingly, as described above, body 306 may also be machined so as to include all such features, including axially extending grooves 320.

Figure 23:
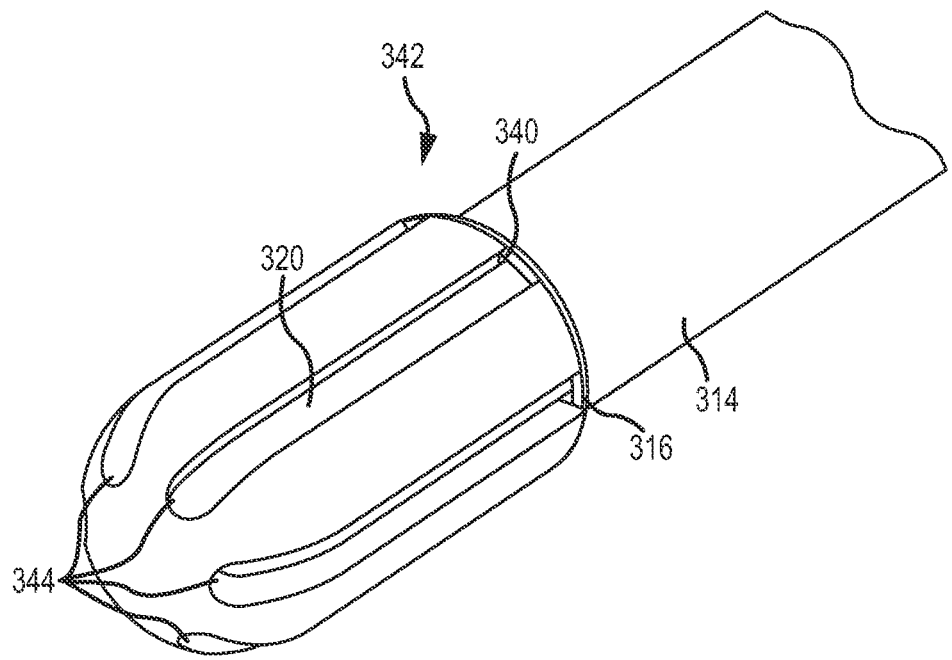
FIG. 23 is an isometric view of a sub-assembly of FIG. 19 in a second stage of manufacture.

FIG. 23 is an isometric view of a further sub-assembly 342 in a further stage of manufacture. The next step in the manufacture of tip electrode assembly 301 includes assembling the casing 310 over and onto body 306, which assembling step includes a number of sub-steps. The first sub-step involves sliding washer 316 over the shank portion 336. The second sub-step involves inserting the shank cover 314 over the shank portion 336 and then advancing the distal edge thereof until washer 316 is seated against shoulder 340, with the shank cover flange seated against washer 316. As shown, grooves 320 include distal-most portions, designated as portions 344.

Figure 24:
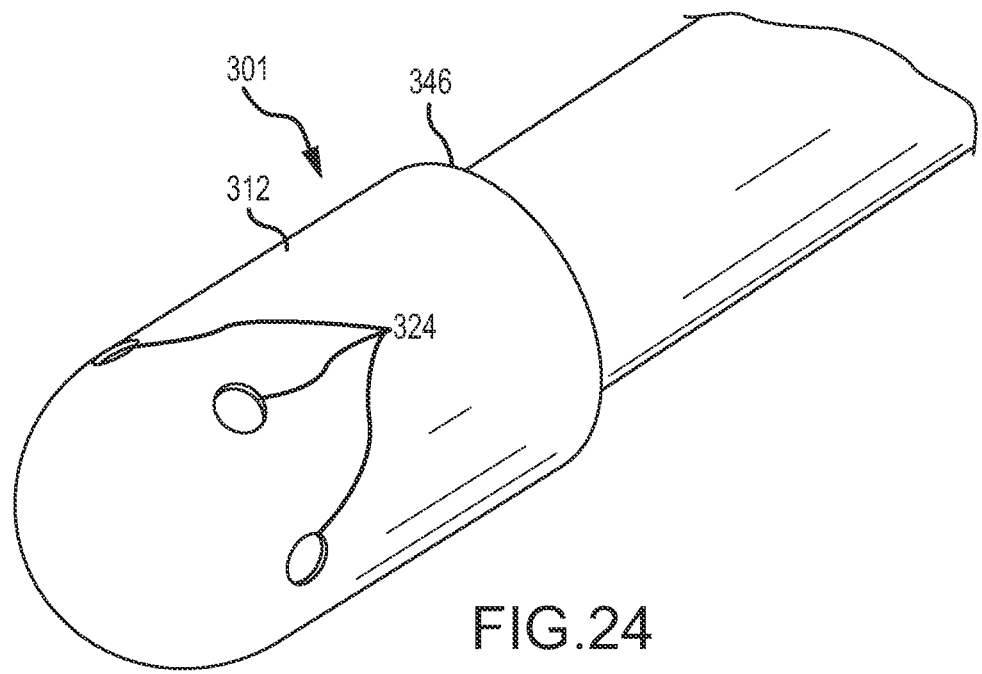
FIG. 24 is an isometric view of the fully manufactured tip electrode assembly.

FIG. 24 is an isometric view of tip electrode assembly 301. The next sub-step includes inserting the tip cap 312, which includes first aligning the apertures 324 with the grooves 320. After the tip cap 312 has been fully inserted, the proximal edge 346 thereof is rolled (or crimped) and then welded (e.g., laser welded), in a manner that may be the same as described and illustrated above (FIG. 6) in connection with catheter 100. A further step, for example, in a method to manufacture catheter 300, the electrical connections (e.g., for ablative energy) and irrigation supply connections are made between the electrode assembly and the catheter shaft. Finally, the passive proximal end portion of tip electrode assembly 301 is coupled to the distal end portion of the catheter shaft.

FIGS. 26-30 are directed to a fourth electrode assembly embodiment and FIG. 26 in particular is a side view of a single-use magnetically-guided, irrigated RF ablation catheter 400 having a distal tip assembly 402 that includes a multi-segment tip positioning magnet body 404. The distal portion of a shaft 406 of catheter 400 is shown in phantom while the proximal portion of catheter 400 (e.g., the proximal hub, etc.) has been omitted for clarity, in particular for visibility of the outer surface of magnet body 404. It should be understood that generally conventional catheter structures (e.g., shaft, handle, irrigation tube, etc.) may be used in connection with tip electrode assembly 402, with the exception that the distal shaft section of catheter 400 may also comprise a relatively flexible segment, like segment 108 described above in connection with catheter 100. Further, it should be understood that embodiments of catheter 400 may, and typically will, include additional structural and functional features that have been omitted for clarity (e.g., irrigation fluid feed tube, temperature sensor(s) and associated connecting wires, etc.).

FIG. 27 is an end view of magnet body 404, showing a central through bore 408. Bore 408 is configured in size and shape to accommodate an irrigation fluid delivery tube 410 (best shown in FIG. 26) configured to transport irrigation fluid 208 from a proximal end portion 412 of magnet body 404 to a distal end portion 414. The tube 410 is configured to mate with a corresponding inlet of a manifold portion (not shown) of an irrigated ablation tip 416, shown in block form in FIG. 26. Irrigated tip 416 may comprise conventional configurations and materials (e.g., a Platinum (Pt) material ablation tip having a distal ablation surface as well as one or more irrigation ports for delivery of irrigation fluid, which may be distal exit ports, side exit ports and angled exit ports). In an embodiment, the magnet body 404 has a substantially continuous outer surface 418. Note that the magnet body 404 is isolated from irrigation fluid 208 as well as bio-fluids, thereby preventing undesirable corrosive effects described above. It should be understood that a non-irrigated electrode tip may be substituted for tip 416 (i.e., for a non-irrigated ablation catheter or non-irrigated electrode catheter for non-ablation purposes, such as for mapping or other diagnostic or therapeutic purposes).

Figure 28:
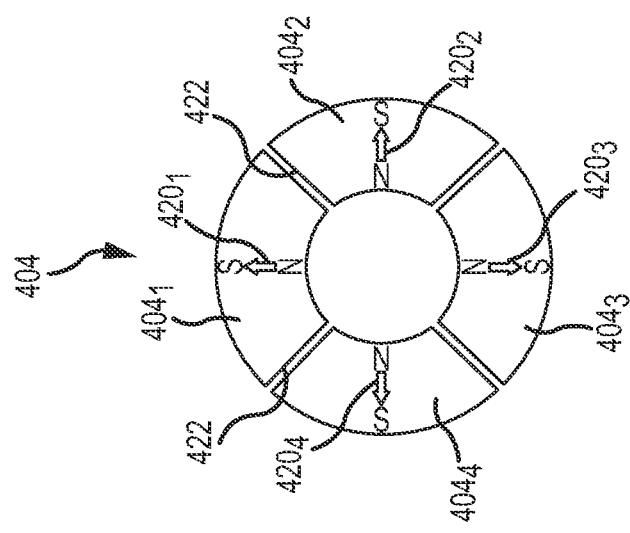
FIG. 28 is an enlarged view of the multi-segment magnet of FIG. 27.

FIG. 28 is an enlarged view of FIG. 27 showing magnet body 404. Multi-segment magnet body 404 includes a plurality of axially-extending, circumferential segments. FIG. 28 shows a four segment embodiment, having segments (clockwise) $404_1$, $404_2$, $404_3$ and $404_4$ although it should be understood that a fewer or a greater number of segments may be employed (e.g., a two segment magnet, a six segment magnet, a thirty-six segment magnet, etc.). In one embodiment, each segment is individually magnetized to establish radially-directed magnetic orientations shown as orientations $420_1$, $420_2$, $420_3$ and $420_4$. In FIG. 28, the segments $404_1$, $404_2$, $404_3$ and $404_4$ are magnetized and arranged relative to each other so that the respective North (N) poles face in a radially-inwardly direction. Through the foregoing arrangement, the collective magnetic field lines emanating from the North poles are combined, thereby increasing a peak magnetic field strength produced by the multi-segment magnet body 404 compared to a non-segmented magnet. The circumferential extent (i.e., in degrees) of each segment is such that, when assembled, the plurality of segments extend through approximately 360 degrees. Each segment includes respective engagement surfaces 422 (shown for segment $404_1$ only). The multi-segment magnet body 404 includes an axial length and an outside diameter. In the illustrated embodiment, an aspect ratio of the axial length to the outside diameter is several times greater than one, although it should be understood that in alternate embodiments, an aspect ratio of one or less may be provided, particularly in view of the increased, peak magnetic field strength (B) levels achieved by a multi-segment magnet body.

Figure 29:
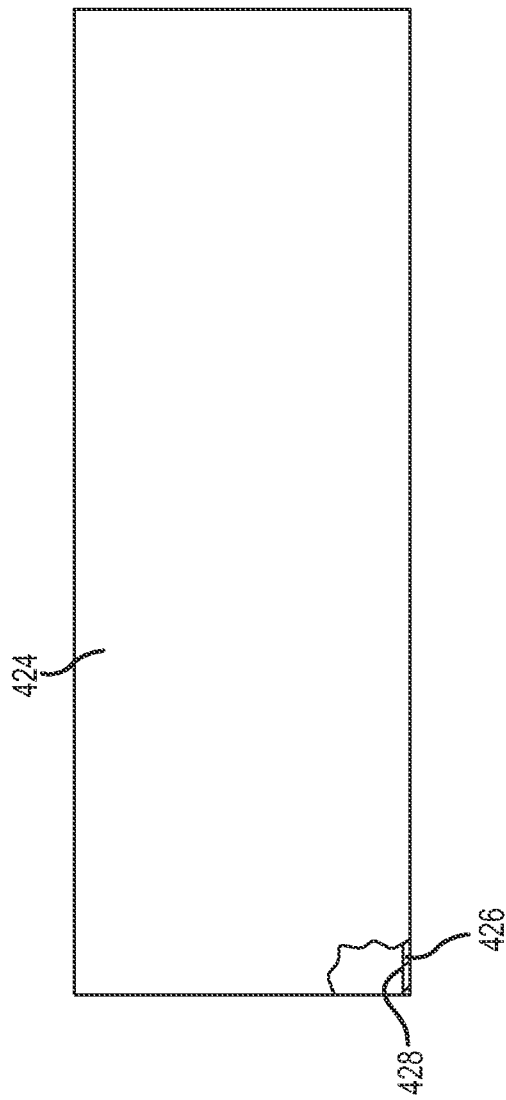
FIG. 29 is a sleeve used in a method of manufacturing the multi-segment magnet of FIGS. 26-28.

FIG. 29 shows a thin-walled cylindrical retention sleeve 424 used in an embodiment for manufacturing a multi-segment magnet body 404 or alternatively an alternating pole magnet body such as magnet body 446 (best shown in FIG. 32 below). The sleeve 424 includes a relatively thin-wall 426 whose inner surface 428 is coated with a lubricant (e.g., polytetrafluoroethylene, commercially available under the trade designation TEFLON® from E.I. du Pont de Nemours and Company, Wilmington, Del., U.S.A.). The lubricant is selected so as to inhibit adhesion of an adhesive (more below) to the inside wall of the sleeve 424 when binding the individual segments together. The sleeve 424 has an inside diameter corresponding to an outside diameter of the multi-segment magnet body 404.

With reference to FIG. 29, a method of manufacturing a multi-segment magnet body includes a number of steps. The first step involves providing a sleeve (i.e., such as sleeve 424) for retaining the plurality of individual segments during adhesive cure. The second step involves producing a plurality of segments each comprising magnetic material and each having a circumferential extent such that the plurality of segments, collectively, extend through about 360 degrees. In this regard, a sub-step involves first producing an intermediate magnet body. The intermediate magnet body may comprise the same magnetic materials as described above in connection with magnet body 130 and which may include the same or substantially similar method steps described above in connection with magnet body 130 (i.e., compaction, sintering, machining and magnetizing), with the exception that the machining and magnetizing steps will be somewhat different, with different shapes, features and dimensions, as described further below.

In particular, after a sintered slug has been machined to a desired outside diameter and after producing a through-bore 408 (e.g., drilling), the individual magnet segments $404_1$, $404_2$, $404_3$ and $404_4$ may be produced by longitudinally cutting the intermediate magnet body (workpiece).

The third step of the method of manufacturing includes magnetizing the plurality of segments in accordance with a predetermined magnetization strategy. The magnetization strategy may be to produce either a uni-polar multi-segment magnet body (e.g., like magnet body 404 shown in FIG. 28) or alternately to produce an alternating pole multi-segment magnet body (e.g., like magnet body 446 shown and described below in connection with FIGS. 32-35A-35B). In the case of a uni-polar multi-segment magnet body, all of the plurality of segments are magnetized the same way so as to establish the same radially-directed magnetic orientation (e.g., with the N pole directed radially inwardly and the S pole radially outwardly) in each segment. In the case of an alternating pole multi-segment magnet body, however, a number of sub-steps are performed. The sub-steps include first magnetizing half of the plurality of segments in a first radially directed magnetic orientation and second magnetizing the remaining half of the plurality of segments in a second radially directed magnetic orientation that is opposite that of the first magnetic orientation. In an embodiment, the first magnetic (radial) orientation may be where the North (N) magnetic pole resides on the radially-innermost portion of the segment and the South (S) magnetic pole resides on the radially-outermost portion of the segment (e.g., this magnetic orientation is shown in segment 4041 in FIG. 28), while the second magnetic orientation is opposite (i.e., N pole resides on the radially outermost portion of the segment and the S pole resides on the radially innermost portion, such as segment 4462 in FIG. 32).

The fourth step in the method of manufacturing involves applying an adhesive to the respective engagement surfaces 422 (best shown in FIG. 28) of the individual segments of the multi-segment magnet body. The adhesive may comprise suitable biocompatible medical grade adhesives, and may comprise epoxy, cyanoacrylate (CA), or other suitable adhesives curable through any suitable mechanisms.

The fifth step involves inserting the segments, having the applied adhesive, into the retention sleeve 424 in a predetermined arrangement. In a uni-polar (e.g., magnet body 404) magnet embodiment, the predetermined arrangement is an arrangement wherein all the segments, including adjacent segments, have the same magnetic orientation. In an alternating pole magnet embodiment (e.g., magnet body 446 in FIG. 32), the predetermined arrangement is an arrangement wherein adjacent segments in the multi-segment magnet body have the opposite magnetic orientation. In the uni-polar multi-segment magnet embodiment, the arrangement of the segments, in view of the individual magnetic orientations, will produce a repulsive force tending to oppose the radially-inward assembly of the individual segments. The sleeve 424 is thus used to force the segments together, despite the repulsive, opposing force. The sleeve 424 is sized so that its inside diameter is just slightly larger (i.e., essentially corresponds to) that the outside diameter of multi-segment magnet, ensuring a tight fit of the individual segments while the adhesive cures.

The sixth step involves curing the adhesive to thereby bind the segments together to produce the multi-segment magnet body. Once the adhesive has cured, the completed multi-segment magnet body may be removed from the sleeve 424. The lubricant on the inside surface 428 of the sleeve 424 inhibits adhesion of the adhesive to the inside surface of the sleeve, thereby facilitating removal of the completed multi-segment magnet from the sleeve 424.

Figure 30:
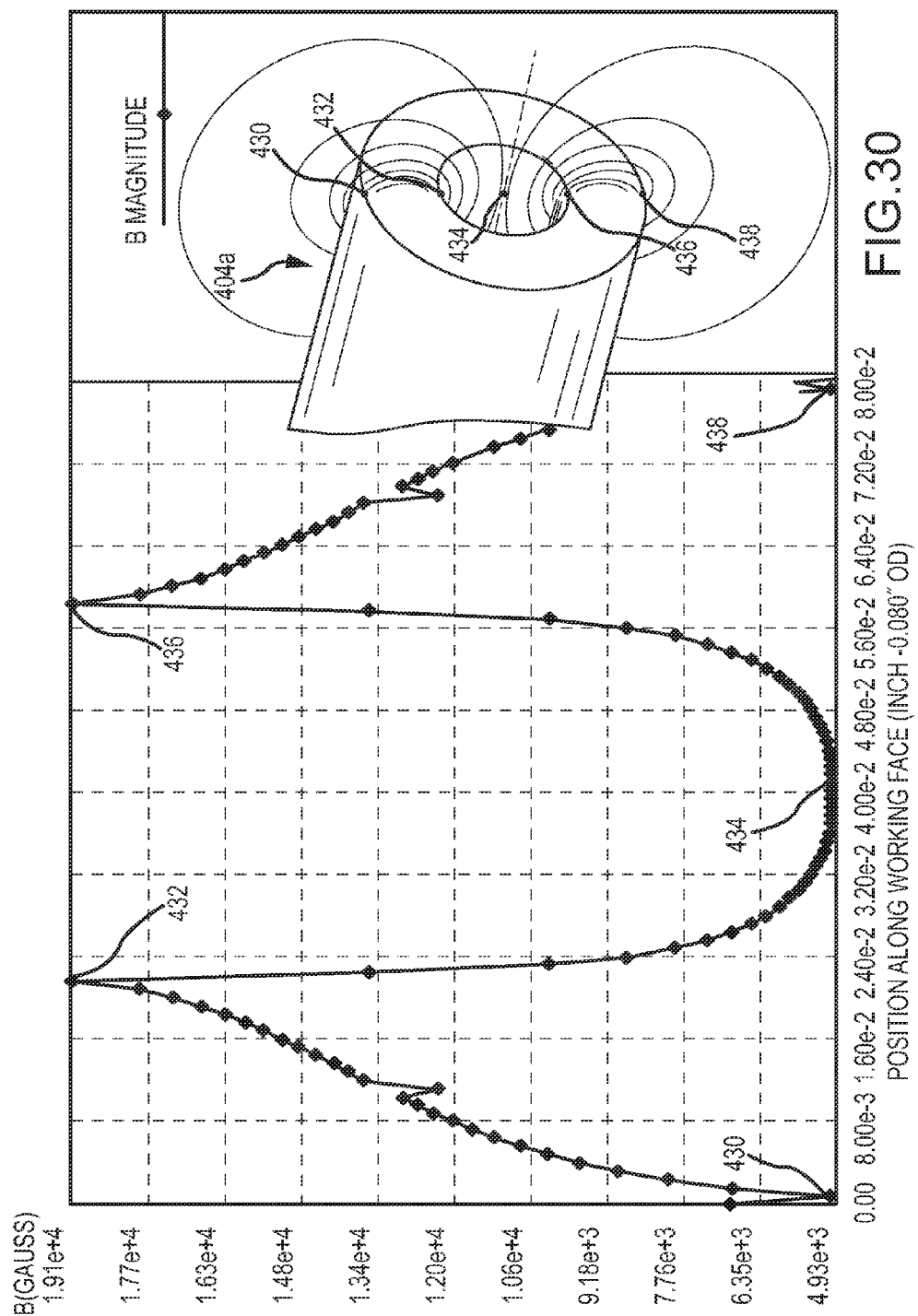
FIG. 30 is a chart showing magnetic field strength of a multi-segment tip positioning magnet.

FIG. 30 is a chart showing the improved magnetic field strength produced in accordance with a multi-segment magnet embodiment. FIG. 30 illustrates the modeled magnetic field strength of a six segment magnet body 404a, having exemplary dimensions of 0.080" outside diameter (OD)× 0.036" inside diameter (ID)×0.500" axial length. As shown, the field strength B (in gauss) is plotted as a function of a position along a working face of the multi-segment magnet body 404a. At positions 430, 438, roughly corresponding to the twelve o'clock and six o'clock positions, the developed field strength is about 4,900 gauss. However, as the position approaches the center bore 408, the field strength increases (e.g., at positions 432, 436) to a peak of about 19,000 gauss. In the center of the bore (i.e., at position 434), the field strength decreases again to about 4,900 gauss. The magnetic field strength produced by the multi-segment configuration is a number of times greater than conventional, unitary approaches, which may produce for similar configurations (e.g., as to materials, dimensions, etc.) a magnetic field strength (B) of about 4,000 gauss, for example, only.

One aspect of the improvement provided by a multi-segment magnet results from the respective, individual improvements as to the magnetization of each of the magnet segments. In conventional configurations, an optimum magnetizing window for magnetizing a magnet segment may be between about 10-15 degrees, which is believed to be a result of the relative grain alignment in the magnet material itself.

Figure 31:
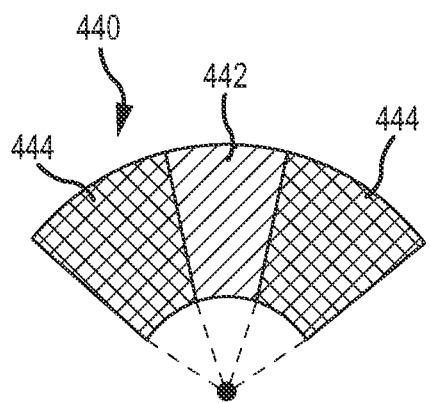
FIG. 31 is a diagrammatic view of a segment of a multi-segment magnet showing different regions of magnetization.

As shown in FIG. 31, assuming a generally cylindrical magnet body is produced so that material grain alignment is generally radially aligned, a magnet segment 440 magnetized by a single magnetizing field may have excellent magnetization in a central sector 442 where the material grain is aligned with such a magnetizing field but may be weaker in outer sectors 444 where the grain alignment, owing to the original radial alignment, would be reduced. As a result, individual magnetization of progressively reduced size (as measured in degrees) segments will result in progressively improved levels of magnetization and thus magnetic field strength production. In one embodiment, a thirty-six segment multi-segment magnet may be provided (i.e., 360°/10 degree sectors). In an alternate embodiment, a twenty-four (24) segment multi-segment magnet may be provided (i.e., 360°/15 degree sectors). Even a two-segment multi-segment magnet will exhibit some measure of improvement.

Figure 32:
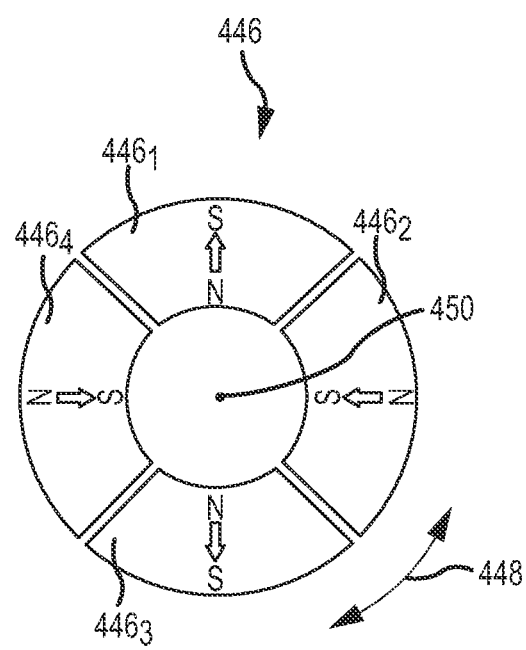
FIG. 32 is an end view of multi-segment magnet having alternating magnetic orientations for adjacent segments.

FIG. 32 is a simplified end view of an alternating pole multi-segment magnet body 446. Multi-segment magnet body 446 includes a plurality of individual magnet segments, which in the illustrated embodiment includes four segments $446_1$, $446_2$, $446_3$ and $446_4$. One difference with multi-segment magnet body 446, as compared to the multi-segment magnets of FIGS. 26-31, is that the magnetic orientation of adjacent segments is not the same, but rather, is opposite so as to produce an alternating pole configuration. In other words, the radially-outermost surface of magnet body 446, taken clockwise, presents the following sequence of magnetic poles: S-N-S-N. Likewise, the radially-innermost surface of magnet body 446, taken clockwise, presents the following sequence of magnetic poles: N-S-N-S. The alternating pole configuration, while in the presence of a suitably configured external magnetic field, may be used to develop rotation of the magnet body 446 in the rotary directions of double-headed arrow 448 about an axis 450, which extends into the paper in FIG. 32. It should be understood that while the exemplary alternating pole, multi-segment magnet body 446 includes four segments, this number is exemplary only and not limiting in nature (i.e., the number of segments may be an even number such as two, four, six, eight, twenty-four, thirty-six, etc.). A suitably configured external magnetic field may involve communication with the external field or field generator, and in addition, may involve having to pulse the externally-generated field to achieve rotation.

Figure 33:
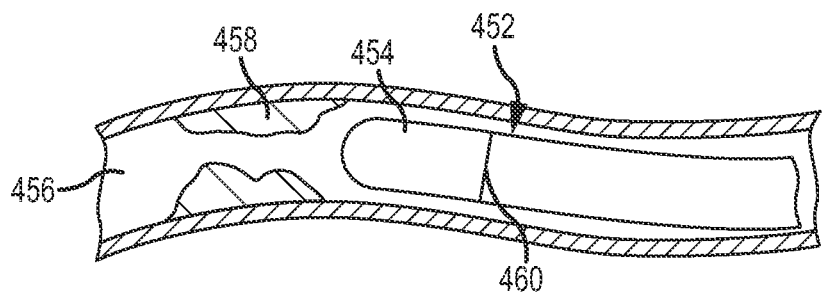
FIG. 33 is simplified cross-section view of a lumen clearing embodiment using an alternating pole multi-segment magnet.

Referring to FIG. 33, in one embodiment, an alternating pole multi-segment magnet may be used in a lumen clearing device, such as a device 452. The device 452 includes a shaft having proximal and distal end portions with a rotatable portion 454 located at the shaft distal end. The portion 454 is rotatable by virtue of inclusion of an alternating pole multi-segment magnet (not shown in FIG. 33), for example, the same or similar to magnet body 446 in FIG. 32. The device 452 is shown in a body lumen 456, such as a vein or an artery of a human, which lumen 456 has an obstruction 458, such as plaque or the like. An external field generator (not shown) may be configured to establish a suitable magnetic field configured to rotate the rotatable portion 454 (i.e., via rotation of the included alternating pole multi-segment magnet) about a main axis. The rotational movement may generally be a reciprocating movement or alternatively a complete revolutionary movement. In the latter case, the device 452 may include a conventional swivel type joint 460 or the like to allow for complete revolutionary movement. The rotatable portion 454 may include an outer clearing structure coupled to move together with the movement of the alternating pole multi-segment magnet. The clearing structure may configured in ways known in the art for effective endovascular obstruction clearing, such as by suitable surface preparation by way of grooves, projections, pockets or holes, surface texturing or roughening, eccentricity of shape or the like, as seen by reference to U.S. application Ser. No. 11/962,738 filed Dec. 21, 2007 entitled ULTRASONIC ENDOVASCULAR CLEARING DEVICE, owned by the common assignee of the present invention, and hereby incorporated by reference in its entirety.

Figure 34:
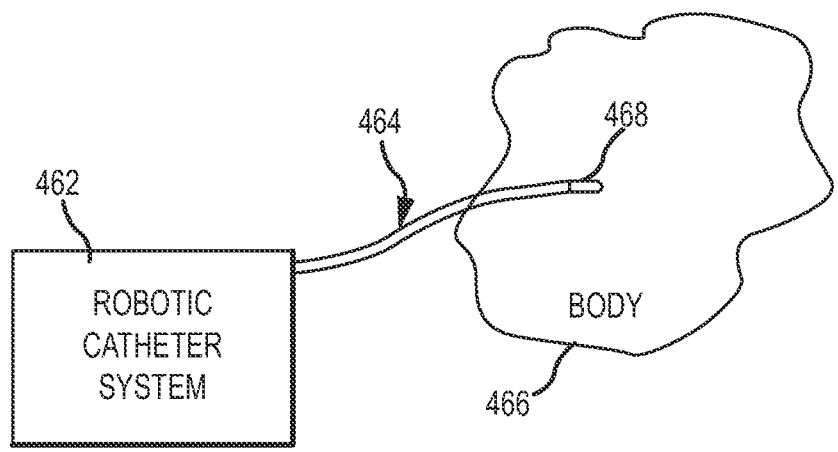
FIG. 34 is a block and diagrammatic view of a robotic catheter system having a distal rotatable portion employing an alternating pole multi-segment magnet.

Referring to FIG. 34, in another embodiment, an alternating pole multi-segment magnet may be incorporated into a catheter configured for use with a robotic catheter system, such as the robotic catheter system in U.S. application Ser. No. 12/751,843 filed Mar. 31, 2010 entitled ROBOTIC CATHETER SYSTEM, owned by the common assignee of the present invention and hereby incorporated by reference in its entirety. As shown in FIG. 34, a robotic catheter system 462 is configured to manipulate and maneuver a catheter 464 within a lumen or a cavity of a human body 466. The catheter 464 in particular may include a shaft having proximal and distal end portion as well as a rotatable portion 468 at the shaft distal end. The rotatable portion 468 is configured for rotation about a main axis thereof (i.e., axis A in FIGS. 35A-35B) and includes (i) an alternating pole multi-segment magnet body (such as magnet body 446 in FIG. 32, not shown in FIGS. 34-35A, 35B) and (ii) a functional feature block configured to perform one of a diagnostic or therapeutic function.

For context, a robotic catheter system such as that referred to above may include a virtual rotation feature of the distal end portion of the catheter, implemented using, for example, four steering wires to achieve omni-directional distal end bending without actual rotation of the catheter shaft. In the system referred to above, the steering wires are advanced/withdrawn using cartridges affixed to a working or control arm external to the body. Certain diagnostic and/or therapeutic features, such as either an imaging modality or an ablation surface, however, may have a directionality characteristic where actual rotation of the distal end portion would be desirable so as to more properly configure the functional feature block for its intended use (e.g., an imaging functional block that needs to be rotated so that its line-of-sight is directed to a body feature of interest or an ablation functional block that needs to be rotated so that an ablative energy delivery trajectory from an ablative surface is directed to the tissue to be ablated, etc.).

Figure 35A:
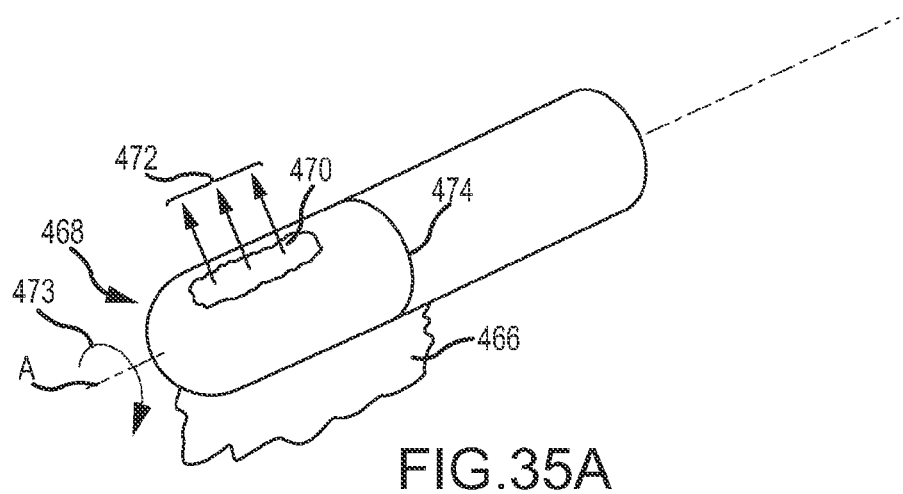
FIGS. 35A-35B are simplified isometric views of the distal rotatable portion of the catheter of FIG. 34, which includes a functional feature block, in first and second rotary positions, respectively.
Figure 35B:
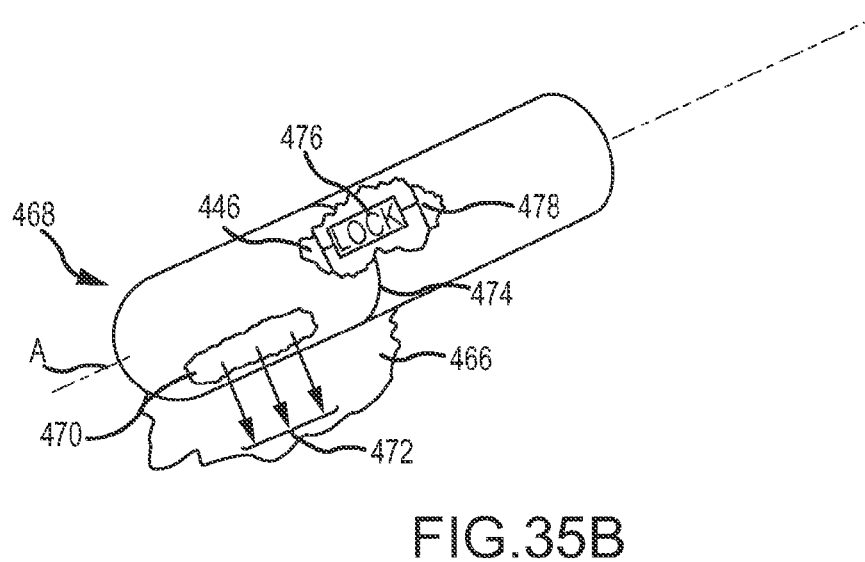

FIGS. 35A-35B are isometric views of rotatable portion 468 in a first, initial rotary position and a second, final rotary position, respectively. In FIG. 35A, rotatable portion 468 includes a functional feature block 470 (e.g., an imaging modality or an ablation surface) having a directionality characteristic (e.g., line-of-sight, trajectory of ablative energy delivery) represented by arrows 472. In FIG. 35A, the portion 468 is shown in a first, initial rotary position. However, it would be desirable to rotate portion 468 such that the directionality arrows 472 are directed toward body 466, which, for example, may be an imaging region of interest or an ablation target tissue region.

The distal rotatable portion 468 includes an alternating pole multi-segment magnet (e.g., magnet body 446 in FIG. 32) and functional feature block 470, which are configured to rotate together on common axis A when the alternating pole multi-segment magnet is rotates. As described, the alternating pole multi-segment magnet is configured to respond to an externally applied magnetic field so as to rotate about a magnet axis thereof (which may be coincident with the common axis A). In FIG. 35A, to rotate portion 468 (and thus also the functional feature block 470) about axis A so that the directionality arrows point to the desired target (i.e., body 466), the rotatable portion 468 is rotated in the direction of arrow 473 (clockwise). In an embodiment, catheter 464 may further include a swivel-type joint 474 or the like configured to permit relative rotation between the portion 468 and the catheter shaft.

FIG. 35B shows portion 468 after rotation away from the first rotary position to the second, final rotary position. The functional feature block 470 has likewise been rotated such that the directionality arrows (i.e., arrows 472) now point toward the intended target or region of interest—namely, body 466. Rotating only distal portion 468 is preferable to rotating the entire shaft of catheter 464, or, in the case of a robotic catheter system, rotating the entire control arm on which the steering wire cartridges are located. In addition, once the distal rotatable portion 468 has been rotated in a desired fashion, its rotary position relative to that of the catheter shaft may be selectively locked by lock block 476. Lock block 476 is disposed intermediate the alternating pole multi-segment magnet body 446 and the distal end portion 478 of the catheter shaft. The lock 476 may comprise conventional apparatus known in the art, suitably configured to lock the rotatable portion 468 in a fixed rotary position. The lock 476 may be actuated through known electrical, mechanical (e.g., pull wire) or electromagnetic means.

It should be further understood that the alternating pole multi-segment magnet may also be used in electrode catheter embodiments as described herein (e.g., catheters 100, 200, 300 and 400, particularly catheter 400). For example, the external pulsing described above used to achieve rotation of the rotatable portion may be discontinued. Thereafter, the externally-generated magnetic fields that are generated may be configured to interact with the local field established proximate the distal tip in order to achieve guided movement in three-dimensional space.

The magnetically-guided electrode assembly and catheter embodiments described and depicted herein exhibit improved performance and in the case of the ablation catheters, provide an irrigation function while avoiding the corrosive effects of irrigation fluid on the tip positioning magnet. It should be further understood that while a single tip positioning magnet is depicted in the embodiments herein, that variations directed to multiple magnets are within the spirit and scope of the invention.

It should be understood that ablation catheter systems may, and typically will, include other structures and functions omitted herein for clarity, such as such as one or more body surface electrodes (skin patches) (e.g., an RF dispersive indifferent electrode/patch for RF ablation), an irrigation fluid source (gravity feed or pump), an RF ablation generator (e.g., such as a commercially available unit sold under the model number IBI-1500T RF Cardiac Ablation Generator, available from Irvine Biomedical, Inc) and the like, as known in the art.

It should be further understood that with respect to the irrigated ablation catheters 200, 300, variations are possible with respect to the number, size and placement of the irrigation passageways and corresponding irrigation ports. For example, the invention contemplates catheters configured to provide a plurality of cavities and/or passageways adapted to facilitate the flow of irrigation fluid therethrough to the manifold's outer surface (proximal irrigation) as well as to the distal ablative surface for delivery by the distal irrigation passageways (distal irrigation). The invention further contemplates lateral or side discharge irrigation passageways and ports, angled (e.g., at an acute angle with respect to the main longitudinal axis of the electrode assembly) passageways and ports as well as distal irrigation passageways and ports. The invention still further contemplates various further arrangements, for example, where the irrigation passageways are substantially equally distributed around the circumference of the manifold to provide substantially equal distribution of fluid. It should be understood that the art is replete with various configurations and design approaches for proximal and distal irrigation passageways and ports, and will therefore not be further elaborated upon.

Moreover, although omitted for clarity, the shaft for each of the catheter embodiments may include guideways (i.e., lumens) configured to allow one or more electrical connection wires to pass therethrough. For example, for ablation catheter embodiments, a main ablation power wire will be connected at the proximal end portion (i.e., electrical connector) to an RF ablation generator and routed through such a guideway and then be electrically terminated at the ablation electrode assembly. Likewise, a temperature sensor connection wire (for embodiments having a temperature sensor, for example, thermocouples or thermistors may also follow a similar path as the power wire and then be electrically terminated at the temperature sensor.

Although numerous embodiments of this invention have been described above with a certain degree of particularity, those skilled in the art could make numerous alterations to the disclosed embodiments without departing from the spirit or scope of this invention. All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An electrode assembly for an ablation catheter, comprising:
    a positioning magnet body having a proximal shank portion and a distal portion;
    a manifold including a distribution cavity configured to receive irrigation fluid and an irrigation passageway coupled to said cavity having a distal exit port for delivery of said fluid, said cavity and said passageway being isolated from said body; and
    a unitary outer capsule surrounding said body so as to isolate said body from external bio-fluids, said capsule comprising electrically conductive material including a distal ablation surface.

2. The assembly of claim 1 wherein said body comprises one of a permanent magnet, a permanent magnet comprising rare earth elements and an electro-magnet.

3. The assembly of claim 2 wherein said permanent magnet comprises neodymium iron boron (NdFeB) material.

4. The assembly of claim 1 wherein said manifold includes a tubular portion having said distribution cavity and extending along an axis, said tubular portion including a proximal end portion configured to receive said fluid, said irrigation passageway extending from a distal end portion of said tubular portion, said passageway being in fluid communication with said tubular portion, said manifold being disposed in corresponding recesses in said body.

5. The assembly of claim 4 wherein said corresponding recesses in said body include a centrally-disposed, longitudinally-extending bore configured to receive said tubular portion of said manifold.

6. The assembly of claim 4 wherein said exit port associated with said passageway comprises one of a distal exit port, a side exit port and an angled exit port.

7. The assembly of claim 4 wherein said irrigation passageway is a radially-extending irrigation passageway.

8. The assembly of claim 4 wherein said capsule comprises an electrically conductive coating.

9. The assembly of claim 8 wherein said coating comprises one of:
    (i) a first layer of Ni—Ni material on an outer surface of said body, a second layer comprising gold (Au) material on said first layer and a third layer comprising platinum (Pt) material on said second layer; and
    (ii) a first layer of Ni—Ni material on an outer surface of said body, a second layer comprising titanium (Ti) material on said first layer and a third layer comprising platinum (Pt) material on said second layer.

10. The assembly of claim 1 wherein said body and said manifold extend along an axis wherein said irrigation passageway is an axially-extending irrigation passageway.

11. The assembly of claim 1 wherein said capsule includes (i) a cup-shaped tip cap configured to cover said distal portion of said body, and (ii) a cylindrical-shaped shank cover configured to surround said shank portion, said tip cap including at least one aperture corresponding to said irrigation exit port.

12. An electrode assembly for an electrode catheter, comprising:
    a positioning magnet body having a proximal shank portion and a distal portion; and
    a unitary outer casing surrounding said body so as to isolate said body from external bio-fluids, said casing including a cup-shaped tip cap configured to cover said distal portion of said body and a cylindrical-shaped shank cover configured to surround said shank portion of said body, said casing including said cup-shaped tip cap comprising electrically conductive material, said shank cover being configured to receive a distal end portion of a catheter shaft.

13. The assembly of claim 12 wherein said body is one of a permanent magnet, a permanent magnet comprising rare earth elements and an electro-magnet.

14. The assembly of claim 13 wherein said permanent magnet comprises neodymium iron boron (NdFeB) material.

15. The assembly of claim 1 further including a safety line having distal end portion coupled to an inner bore of said body and a proximal end.

16. The assembly of claim 15 wherein said safety line comprises one of liquid crystal polymer (LCP) material and a para-aramid synthetic fiber.

\* \* \* \* \*